the invention provides Natural Killer (NK) cells that have a reduced or ablated Signal Regulatory Protein Alpha (SIRPα-) function when compared to a NK cell having an unmodified SIRPα- function that effectively kills a population of cancer cells that express CD47.

United States Patent
Deuse

(10) Patent No.: US 12,391,923 B2
(45) Date of Patent: Aug. 19, 2025

(54) SIRPα-SILENCED NATURAL KILLER (NK) CELLS

(71) Applicant: The Regents of the University of California, Oakland, CA (US)

(72) Inventor: Tobias Deuse, Burlingame, CA (US)

(73) Assignee: The Regents of the University of California, Oakland, CA (US)

(*) Notice: Subject to any disclaimer, the term of this patent is extended or adjusted under 35 U.S.C. 154(b) by 910 days.

(21) Appl. No.: 17/621,689

(22) PCT Filed: Jun. 24, 2020

(86) PCT No.: PCT/US2020/039220
§ 371 (c)(1),
(2) Date: Dec. 22, 2021

(87) PCT Pub. No.: WO2020/263880
PCT Pub. Date: Dec. 30, 2020

(65) Prior Publication Data
US 2022/0347215 A1    Nov. 3, 2022

Related U.S. Application Data

(60) Provisional application No. 62/866,683, filed on Jun. 26, 2019.

(51) Int. Cl.
| | |
|---|---|
| C12N 5/0783 | (2010.01) |
| A61K 40/15 | (2025.01) |
| A61K 40/42 | (2025.01) |
| A61P 35/02 | (2006.01) |
| C07K 14/705 | (2006.01) |
| C12N 9/22 | (2006.01) |
| C12N 15/11 | (2006.01) |
| C12N 15/86 | (2006.01) |

(52) U.S. Cl.
CPC ............ *C12N 5/0646* (2013.01); *A61K 40/15* (2025.01); *A61K 40/421* (2025.01); *A61P 35/02* (2018.01); *C07K 14/70503* (2013.01); *C12N 9/22* (2013.01); *C12N 15/11* (2013.01); *C12N 15/86* (2013.01); *C12N 2310/20* (2017.05); *C12N 2500/32* (2013.01); *C12N 2500/44* (2013.01); *C12N 2501/2302* (2013.01); *C12N 2501/998* (2013.01); *C12N 2506/45* (2013.01); *C12N 2740/15042* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 4,427,777 A | 1/1984 | Goldstein | |
| 4,609,627 A | 9/1986 | Goldstein | |
| 5,606,042 A | 2/1997 | Smith et al. | |
| 5,633,130 A | 5/1997 | Smith et al. | |
| 5,731,426 A | 3/1998 | Smith et al. | |
| 6,184,017 B1 | 2/2001 | Smith et al. | |
| 8,796,443 B2 | 8/2014 | Khvorova et al. | |

FOREIGN PATENT DOCUMENTS

| | | |
|---|---|---|
| GB | 2211504 | 7/1989 |
| WO | 97/15664 | 5/1997 |
| WO | 1999023210 | 5/1999 |
| WO | 2011146862 A1 | 11/2011 |
| WO | 2017075276 A2 | 5/2017 |
| WO | 2018132783 A1 | 7/2018 |
| WO | 2020263880 A1 | 12/2020 |

OTHER PUBLICATIONS

PCT Search Report and Written Opinion dated Oct. 30, 2020 issued in PCT Application No. PCT/US2020/039220.
Murata et al.. "Anti-human SIRPalpha antibody is a new tool for cancer immunotherapy," Cancer Science, vol. 109, pp. 1300-1306 (2018).
Nath et al. "CD47 Expression in Natural Killer Cells Regulates Homeostasis and Modulates Immune Response to Lymphocytic Choriomeningitis Virus," Front. Immunol., vol. 9, No. 2985, pp. 1-17 (2018).
Pan et al. "Signal Regulatory Protein a Is Associated With Tumor-Polarized Macrophages Phenotype Switch and Plays a Pivotal Role in Tumor Progression," Hepatology, vol. 58, No. 2, pp. 680-691 (2013).
European Supplementary Search report dated Jun. 12, 2023 for EP Application No. 20832595.1.
Kim et al. Association of CD47 with Natural Killer Cell-Mediated Cytotoxicity of Head-and-Neck Squamous Cell Carcinoma Lines, Tumor Biology, vol. 29, pp. 28-34 (2008).
De Pelsmaeker et al. Porcine NK cells display features associated with antigen-presenting cells, Journal of Leukocyte Biology, GB, vol. 103, No. 1, pp. 129-140 (2017).
Bian et al. Cd47-Sirp[alpha] interaction and IL-10 constrain inflammation-induced macrophage phagocytosis of healthy self-cells, Proceedings of the National Academy of Sciences, vol. 113, No. 37, pp. E5434-E5443 (2016).
Li et al. Human iPSC-Derived Natural Killer Cells Engineered with Chimeric Antigen Receptors Enhance Anti-tumor Activity, Cell Stem Cell, Amsterdam, NL, vol. 23, No. 2, pp. 181-192 (2018).
Ray et al. CRISPRed Macrophages for Cell-Based Cancer Immunotherapy, Bioconjugate Chemistry, US, vol. 29, No. 2, pp. 445-450 (2018).

(Continued)

*Primary Examiner* — Daniel E Kolker
*Assistant Examiner* — Peter Johansen
(74) *Attorney, Agent, or Firm* — Kaplan IP Law, P.C.; Jonathan M. Kaplan

(57) ABSTRACT

The invention provides Natural Killer (NK) cells that have a reduced or ablated Signal Regulatory Protein Alpha (SIRPα-) function when compared to a NK cell having an unmodified SIRPα- function that effectively kills a population of cancer cells that express CD47.

Figure 1A:
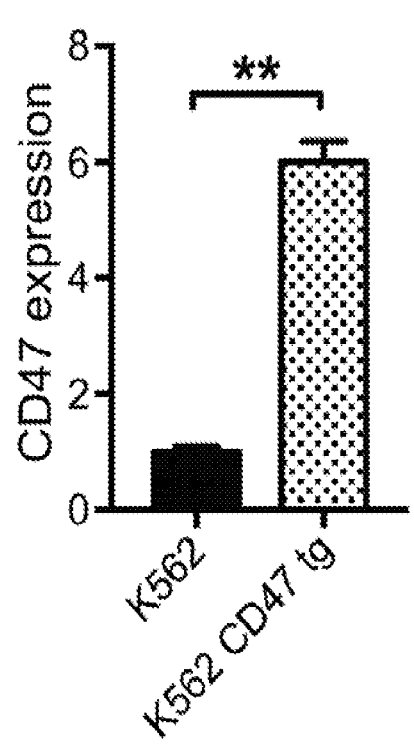

22 Claims, 16 Drawing Sheets
Specification includes a Sequence Listing.

(56) References Cited

OTHER PUBLICATIONS

Chao et al. The CD47-SIRPa Pathway in Cancer Immune Evasion and Potential Therapeutic Implications. NIH Public Access Author Manuscript, pp. 1-13, 2012.
Weiskopf et al. Cancer immunotherapy targeting the CD47/SIRP[alpha] axis, European Journal of Cancer, Elsevier, Amsterdam NL, vol. 76, pp. 100-109, 2017.
Ahmadzada et al. "Fundamentals of siRNA and miRNA therapeutics and a review of targeted nanoparticle delivery systems in breast cancer," Biophys Rev. 10(1):69-86 (2018).
Rinaldi and Wood, "Antisense oligonucleotides: the next frontier for treatment of neurological disorders," Nat. Rev. Neurol. Advance Online Publication (2017).
Shimo et. al. "Design and evaluation of locked nucleic acid-based splice-switching oligonucleotides in vitro," Nucleic Acids Research, 42(12): 8174-8187 (2014).
Fiers et al., Complete nucleotide sequence of SV40 DNA, Nature 273: 113-120, 1978.
Greenaway P. J. et al. Human cytomegalovirus DNA: BamHI, EcoRI and Pst I restriction endonuclease cleavage maps, Gene 18: 355-360, 1982.
Cowan, C. A. et. al. Derivation of Embryonic Stem-Cell Lines from Human Blastocysts, New England J. Med. 350:13, 2004.
Zhou et al. Adenoviral Gene Delivery Can Reprogram Human Fibroblasts to Induced Pluripotent Stem Cells, Stem Cells 27 (11): 2667-74, 2009.
Huangfu, et al. Induction of pluripotent stem cells by defined factors is greatly improved by small molecule compounds, Nature Biotechnol. 26 (7): 795, 2008.
Woltjen et al. piggyBac transposition reprograms fibroblasts to induced pluripotent stem cells, Nature 458 (7239): 766-770, 2009.
Zhou et al. Generation of Induced Pluripotent Stem Cells Using Recombinant Proteins, Cell Stem Cell 8:381-384, 2009.
Barese, Cecilia N. et al. Thymidine Kinase Suicide Gene-mediated Ganciclovir Ablation of Autologous Gene-modified Rhesus Hematopoiesis, Molecular Therapy vol. 20. No. 10 (2012).
Xu, Ling et al. The use of suicide gene systems in vascular cells in vitro, Cell Research 8, 73-78 (1998).
Di Stasi, Antonio et al. Inducible Apoptosis as a Safety Switch for Adoptive Cell Therapy, The New England Journal of Medicine, 365:1673-83 (2011).
Tey, Siok-Keen et al. Inducible Caspase 9 Suicide Gene to Improve the Safety of Allodepleted T Cells after Haploidentical Stem Cell Transplantation, Biology of Blood and Marrow Transplantation, 13:913-924 (2007).
Olsson et al. Universal red blood cells—enzymatic conversion of blood group A and B antigens, Transfusion Clinique et Biologique 11: 33-39, 2004.
U.S. Appl. No. 62/846,399, filed May 10, 2019.
Deuse, T et al. Hypoimmunogenic derivatives of induced pluripotent stem cells evade immune rejection in fully immunocompetent allogeneic recipients, Nature Biotechnology, vol. 37, No. 3, pp. 252-258 (2019).

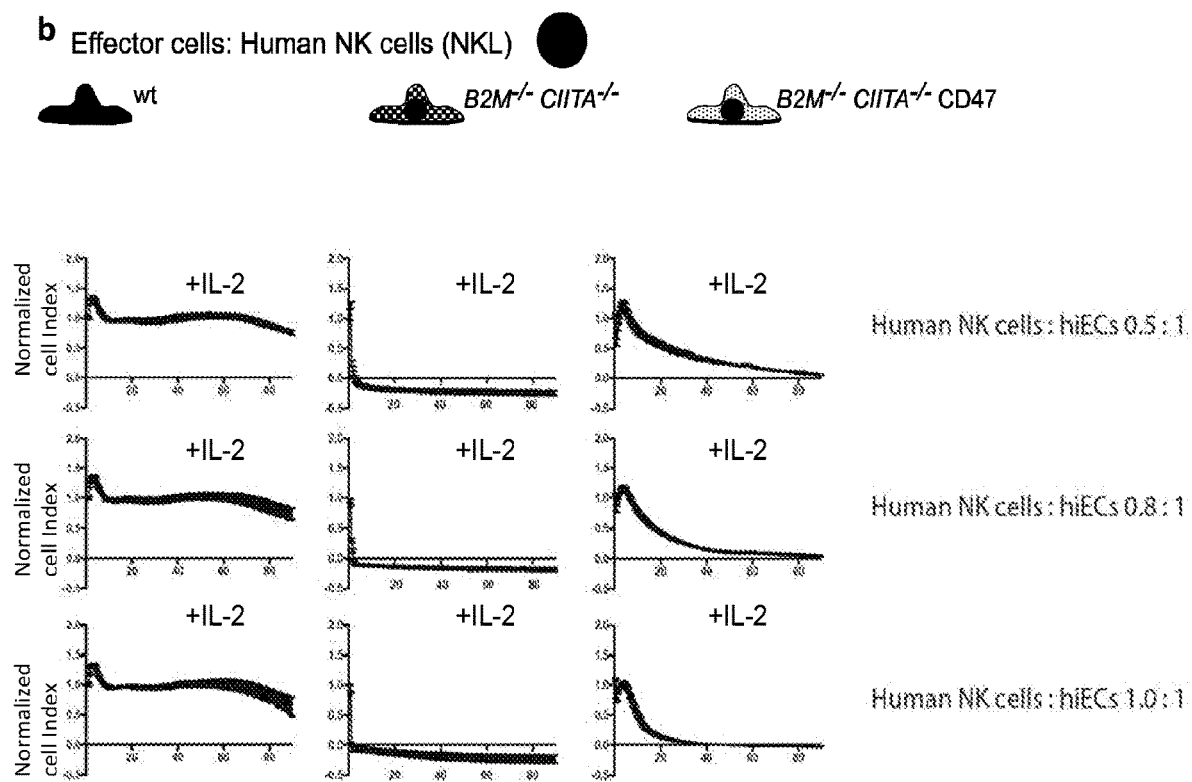

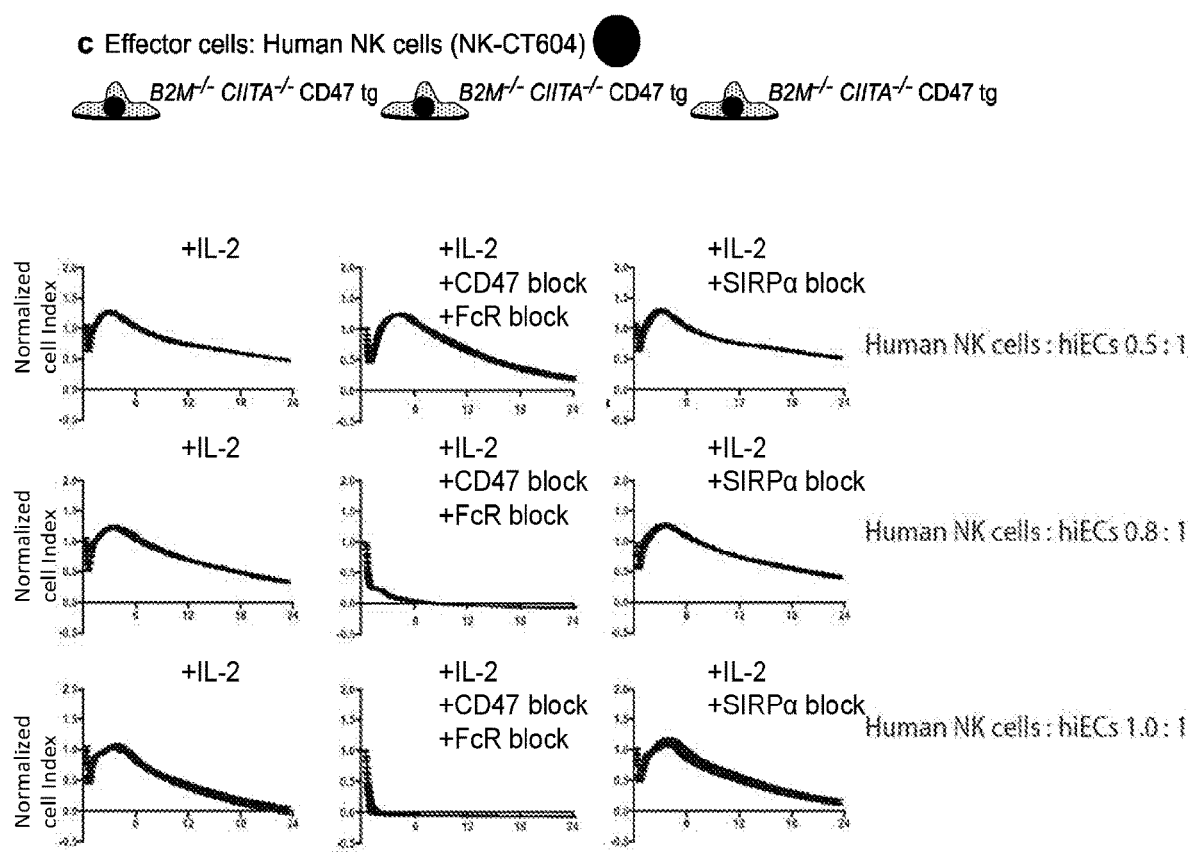

Fig. 7A
Fig. 7B
Fig. 7C
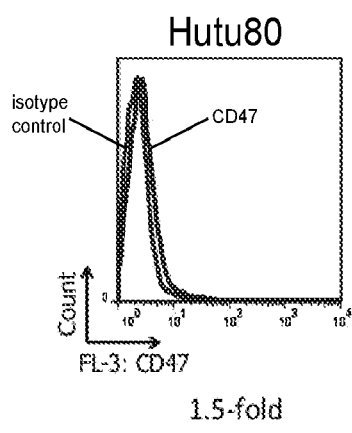
Hutu80
1.5-fold
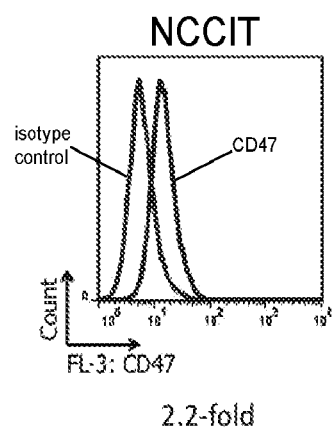
NCCIT
2.2-fold
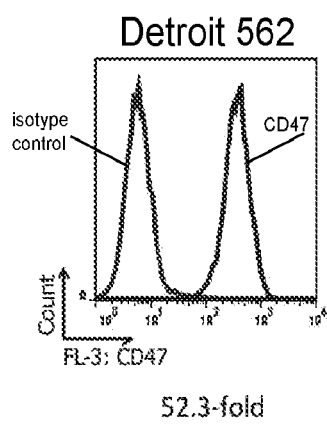
Detroit 562
52.3-fold
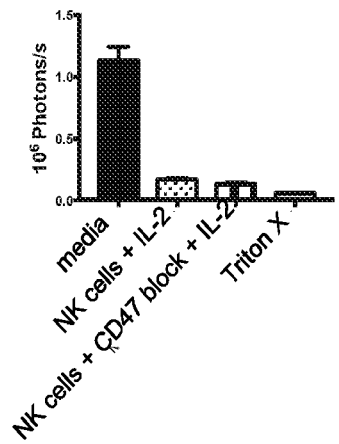
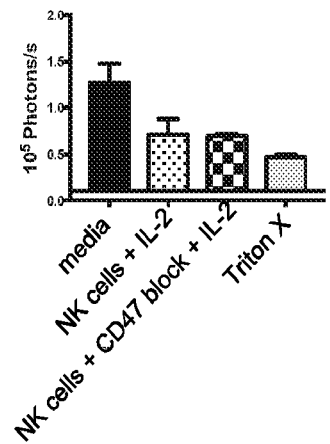
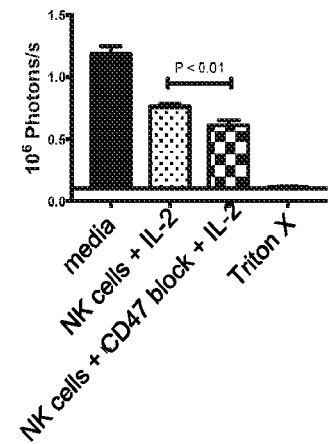

# SIRPα-SILENCED NATURAL KILLER (NK) CELLS

I. CROSS REFERENCE TO RELATED APPLICATIONS

This application is the U.S. National Phase Application of PCT/US2020/039220 filed Jun. 24, 2020 and claims the benefit of U.S. Provisional Application No. 62/866,683, filed on Jun. 26, 2019, which is incorporated herein by reference in its entirety.

I.I SEQUENCE LISTING

The instant application contains a Sequence Listing which has been submitted electronically in ASCII format and is hereby incorporated by reference in its entirety. Said ASCII copy, created on Jul. 14, 2020, is named RUC013W_SL.txt and is 7,501 bytes in size.

II. FIELD OF THE INVENTION

The invention provides Natural Killer (NK) cells that have a reduced or ablated Signal Regulatory Protein Alpha (SIRPα−) function when compared to a NK cell having an unmodified SIRPα− function that effectively kills a population of cancer cells that express CD47.

III. BACKGROUND OF THE INVENTION

Natural killer cells, or NK cells, are cytotoxic lymphocytes critical to the innate immune system. The role NK cells play is analogous to that of cytotoxic T cells in the vertebrate adaptive immune response. NK cells provide rapid responses to virus-infected and cancerous cells. Typically, NK cells become activated by target cells downregulating major histocompatibility complex (MHC) as this is one major inhibitory NK cell signal. NK cell activation triggers cytokine release resulting in lysis or apoptosis. NK cells are unique, because they can recognize stressed cells as they upregulate other stimulatory NK cell signals and do not require prior exposure to certain cell epitopes. This makes them very fast responders. They can also quickly respond to antibody-laden cells because binding of free antibody Fc is a strong stimulatory NK cell signal. NK cells do not require major activation to kill cells that are missing "self" markers of MHC class 1 other than some cytokine exposure like IL-2 or IL-15. This role is especially important because harmful cells that have downregulated or missing MHC I markers cannot be detected and destroyed by other immune cells such as T lymphocyte cells.

NK cells are large granular lymphocytes that are differentiated from the common lymphoid progenitor-generating B and T lymphocytes. They differentiate and mature in the bone marrow, lymph nodes, spleen, tonsils, and thymus, where they then enter into the circulation.

A current approach to treating solid tumors is with chimeric antigen receptor T cells (CAR-T). CAR-T cells are made by removing a patient's own T cells and genetically altering them to attack cancer cells that carry a specific antigen. Currently, CAR-T treatments target CD19 on B cell cancers and a variety of other antigens. CAR-T therapies can be effective but they do not work well against solid tumors. Tumors rebuff T cells that try to enter, inhibit those immune cells that do make it inside, and can curb production of antigens targeted by CAR T cells.

NK cells are a promising alternative because they can attack solid tumors. NK cells have been characterized in the art as lacking SIRPα, a cell-surface receptor that transmits the CD47 "don't eat me" signal from target cells. SIRPα was previously found macrophages.

IV. SUMMARY OF THE INVENTION

The invention provides Natural Killer (NK) cells that have a reduced or ablated Signal Regulatory Protein Alpha (SIRPα) function when compared to a NK cell having an unmodified SIRPα function that effectively kills a population of cancer cells that express CD47. In contrast to NK cell lines studied in the literature, the invention recognizes that, in fact, SIRPα is found on primary NK cells. Reducing or knocking out SIRPα eliminates the transmission of the target cell's CD47 protective "don't eat me" signal from the target cells to the NK cells.

Thus, the invention provides a population of modified Natural Killer (NK) cells, comprising a reduced Signal Regulatory Protein Alpha (SIRPα−) function when compared to an NK cell population having an unmodified SIRPα− function, wherein the modified NK cells effectively kill a population of cancer cells that express CD47 in an in vitro NK assay.

In one aspect of the invention, the cancer cell killing occurs faster than with that of the unmodified NK cell population in the assay. In other aspects of the invention, the modified NK cells are primary NK cells.

In some aspects of the invention, the reduced SIRPα− function results from a genetic modification to the population of modified NK cells. In another aspect, the genetic modification results from a SIRPα− knockout, a regulatory sequence alteration, or a frameshift mutation. In another aspect of the invention, the genetic modification was obtained using a transcription activator-like effector nuclease (TALEN), clustered regularly interspaced short palindromic repeats)/Cas9 (CRISPR-Cas9), or Zinc Finger nuclease technology.

In some aspects of the invention, the reduced SIRPα− function results from an interfering nucleic acid molecule. In other aspects, the interfering RNA is selected from the group consisting of small interfering RNA (siRNA), antisense oligonucleotides (ASO), locked nucleic acids (LNA), splice switching oligonucleotides (SSO), and sno-derived RNA (sdRNA). In some aspects of the invention, the reduced SIRPα− function results from a molecule that binds to the SIRPα− on the surface of the modified NK cells. In other aspects, the molecule is an anti-SIRPα antibody.

In some aspects of the invention, the cancer is selected from the group consisting of acute myeloid leukemia, non-small cell lung cancer, urinary bladder neoplasms, hepatocellular carcinoma, melanoma, Merkel Cell carcinoma, triple negative breast cancer, ovarian cancer, renal cell carcinoma, colorectal cancer, and a sarcoma.

The invention provides a population of modified Natural Killer (NK) cells, comprising a reduced Signal Regulatory Protein Alpha (SIRPα−) function when compared to a NK cell having an unmodified SIRPα− function, wherein the modified NK cells effectively kill a population of hypoimmune cells that express CD47 in an in vitro NK assay. In one aspect, the NK cells are derived from an induced pluripotent stem cell (IPSC). In another aspect, the NK cells are derived from an embryonic stem cell (ESC).

In another aspect of the invention, the NK cells comprise a chimeric antigen receptor (CAR-NK).

The invention provides a method of treating cancer, comprising administering the population of modified NK cells of the invention to a subject. In some aspects, the subject is selected from the group consisting of a human, mouse, rat, cat, dog, rabbit, guinea pig, hamster, sheep, pig, horse, bovine, and non-human primate. In other aspects, the cancer is selected from the group consisting of acute myeloid leukemia, non-small cell lung cancer, urinary bladder neoplasms, hepatocellular carcinoma, melanoma, Merkel Cell carcinoma, triple negative breast cancer, ovarian cancer, renal cell carcinoma, colorectal cancer, and a sarcoma.

The invention provides a method of making the population of modified NK cells disclosed herein, comprising modifying a SIRPα+NK cells to become SIRPα– using a transcription activator-like effector nuclease (TALEN), clustered regularly interspaced short palindromic repeats)/Cas9 (CRISPR-Cas9), or Zinc Finger nuclease technology. In one aspect, the SIRPα protein has at least a 90% sequence identity with SEQ ID NO: 1. In a preferred aspect, the SIRPα protein has the sequence of SEQ ID NO: 1

The invention provides a method of making the population of modified NK cells disclosed herein, comprising downregulating a SIRPα expression in the population of modified NK cells using small interfering RNA (siRNA), antisense oligonucleotides (ASO), locked nucleic acids (LNA), splice switching oligonucleotides (SSO), or sno-derived RNA (sdRNA).

V. BRIEF DESCRIPTION OF THE DRAWINGS

Figure 1B:
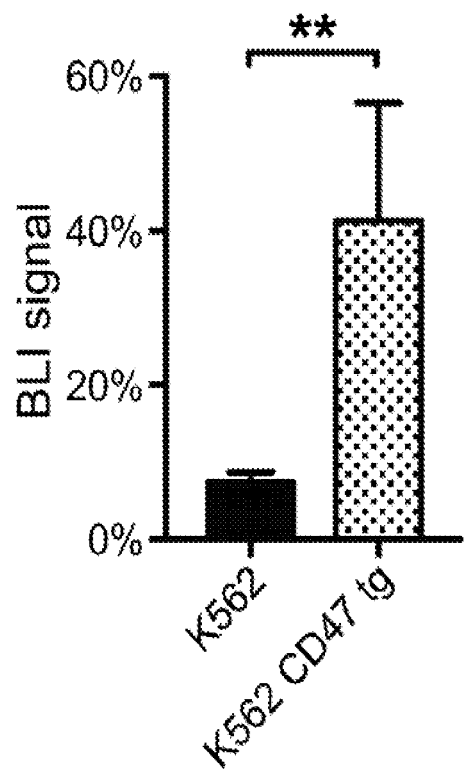

FIG. 1A shows K562 cancer cells overexpressing CD47 under a constitutive promoter with an approximately 6-fold increased expression levels. FIG. 1B shows CD47-overexpressing K562 cells that have been transduced to express firefly luciferase and cultured with primary NK cells. The K562 killing was quantified by a drop in BLI signal. CD47-overexpressing K562 were significantly protected from primary NK cell killing when compared to the K562 cells that do not overexpress CD47 (mean±s.d., 3 independent experiments per group).

Figure 2A:
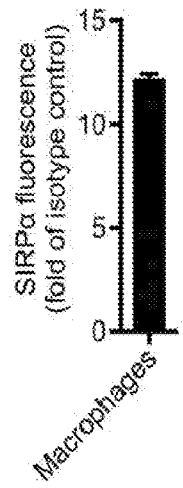
Figure 2B:
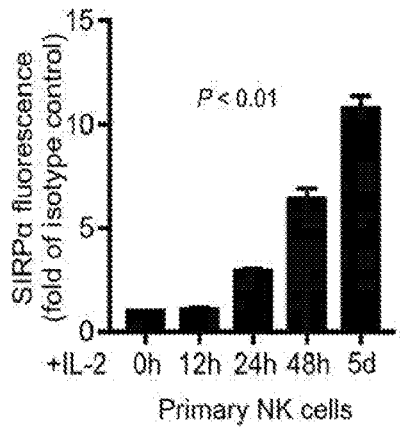
Figure 2C:
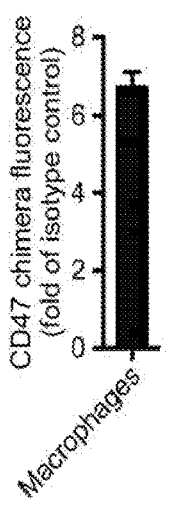
Figure 2D:
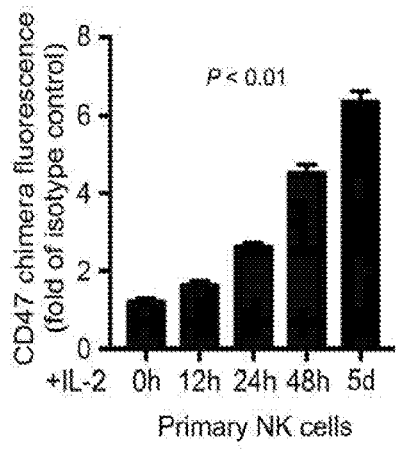

SIRPα is expressed on human NK cells. SIRPα expression was examined on macrophanges and primary NK cells using flow cytometry. FIG. 2A shows SIRPα on macrophages, a known expressor. (mean±s.d., 4 independent experiments per group). FIG. 2B shows IL2-inducible SIRPα expression on primary human NK cells. Primary NK cells isolated from PBMCs showed very low levels of SIRPα expression. With IL2 stimulation, SIRPα expression was significantly and progressively upregulated over 5 days. FIG. 2C shows CD47 binding to macrophages. Macrophages are known to bind CD47. FIG. 2D shows a CD47 chimera binding to primary NK cells over time. CD47 binding was very low without IL2 and significantly and progressively increased over 5 days.

Figure 3A:
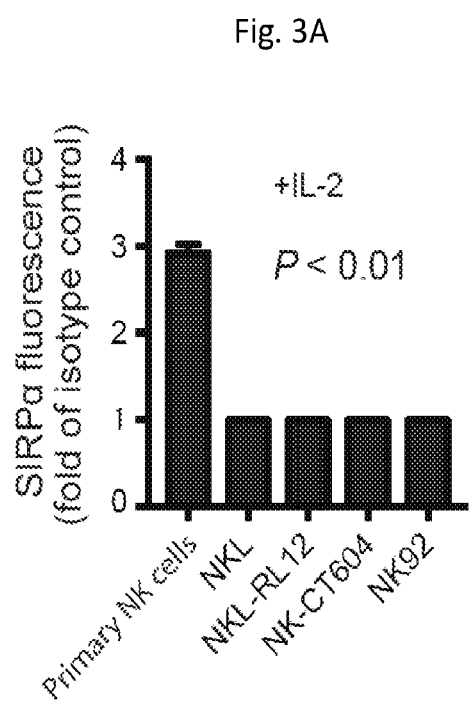
Figure 3B:
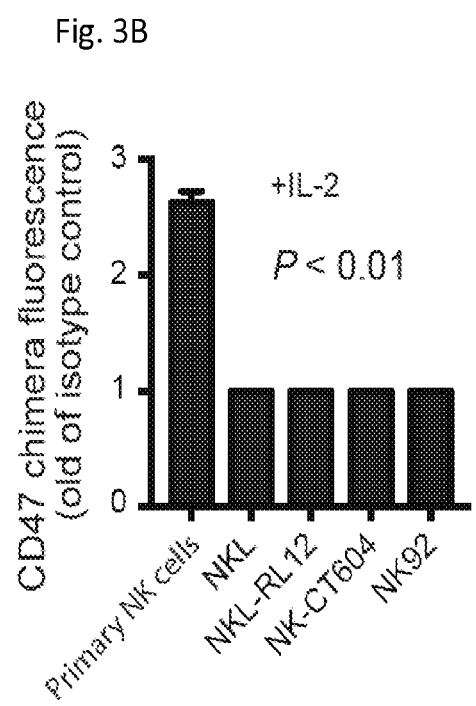

FIG. 3A shows SIRPα expression on primary NK cells and on 4 established NK cell lines in the presence of IL2. All 4 NK cell lines screened (NKL, NKL-RL12, NK-CT604, NK92) showed no SIRPα expression. FIG. 3B shows that while primary NK cells can bind CD47 with IL2 stimulation, all 4 screened NK cell lines showed no CD47 binding. (mean±s.d., 4 independent experiments per group).

Figure 4A:
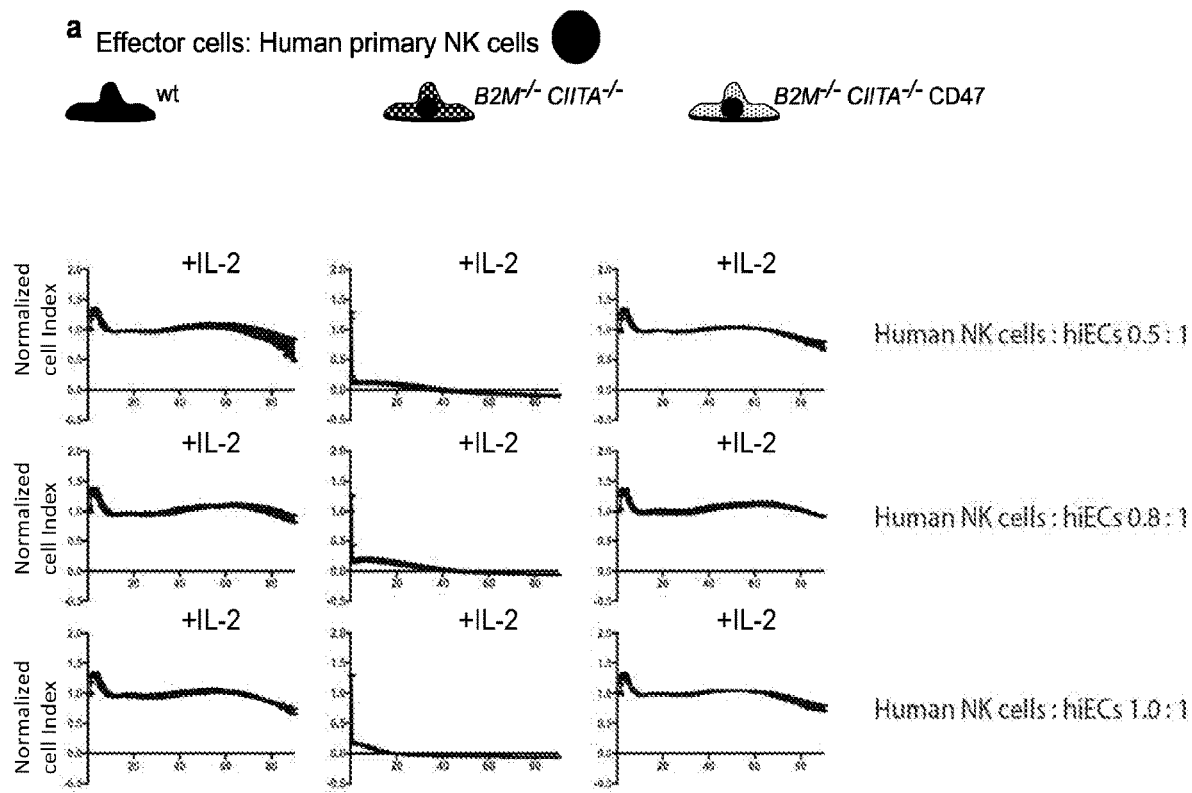

FIG. 4A shows that human wild-type induced endothelial cells (hiEC) were not killed by primary NK cells. hiECs lacking HLA class I and HLA class II (B2M–/–CIITA –/–) were quickly and efficiently killed by primary NK cells. When the HLA class I and HLA class II-deficient target cells, however, additionally included CD47, they were not killed. FIGS. 4B-4E show the same groups of target hiECs with NK cell lines. Again, wt hiECs were not killed and B2M–/–CIITA –/– were very rapidly killed. When the target cells expressed CD47 (CD47 tg), however, they were killed by all 4 NK cell lines in contrast to FIG. 4A where they survived a primary NK cell challenge. The kinetics of target cell killing, however, was mildly changed towards a mildly slower killing (mean±s.d., 3 independent experiments per group).

Figure 5A:
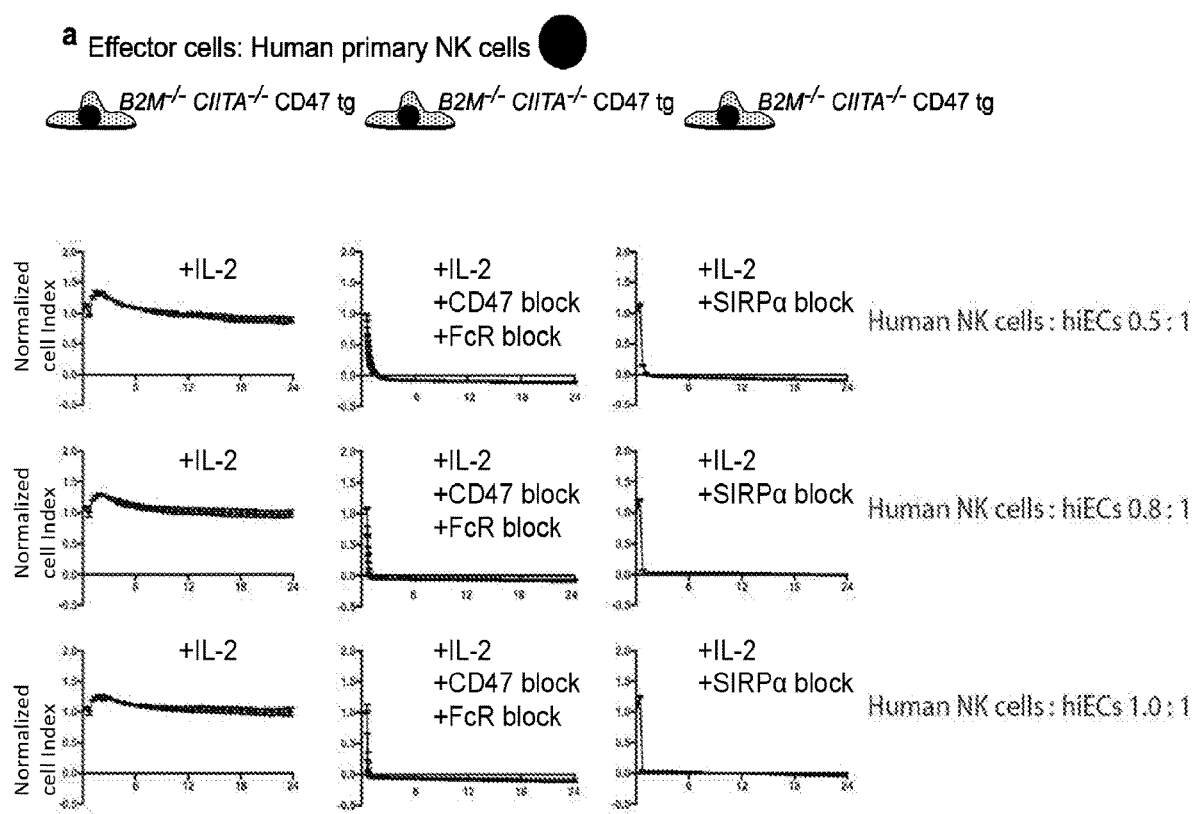
Figure 5B:
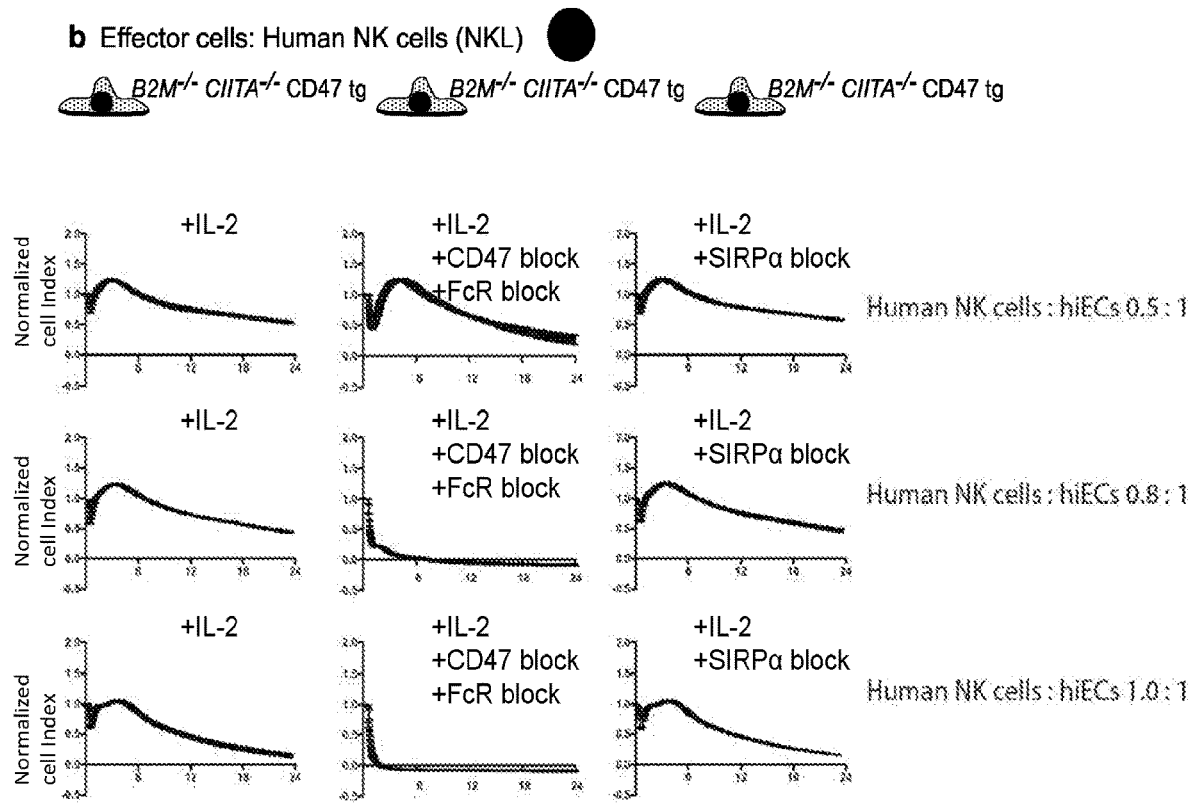

FIGS. 5A-5E shows killing curves of B2M–/–CIITA –/–CD47 tg hiECs from primary NK cell and NK cell line killing in the presence of IL2. In some experiments the CD47– SIRPα binding was prevented using specific antibodies against CD47 or SIRPα. FIG. 5A shows that primary NK cells very quickly killed the target cells if either CD47 or SIRPα was blocked. An in vitro impedance assay was used. FIG. 5B shows the NKL cell line. FIG. 5C shows the NK-CT604 cell line. Figure SD shows the NK-RL12 cell line. Figure SE shows the NK-92 cell line. Together, blocking neither CD47 nor SIRPα markedly changed the killing characteristics of the 4 NK cell lines (mean±s.d., 3 independent experiments per group).

Figure 6A:
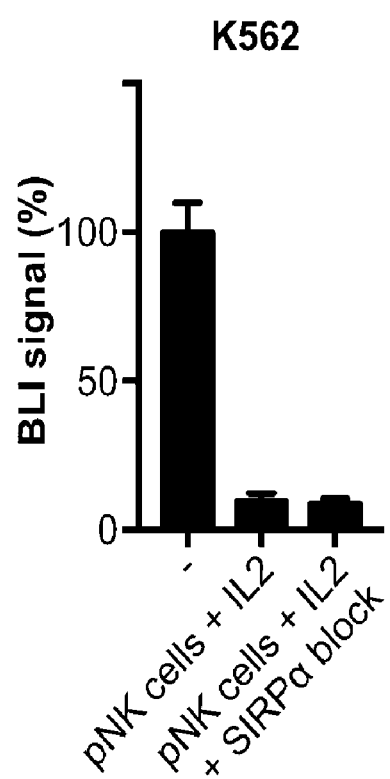
Figure 6B:
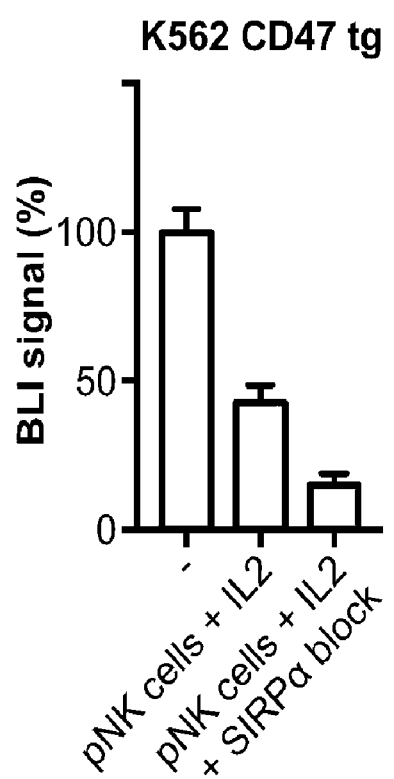

FIGS. 6A-6B shows the killing of firefly luciferase-expressing K562 by primary NK cells. FIG. 6A shows that K562 are very effectively killed if primary NK cells are stimulated with IL2. SIRPα blockage did not affect target cell killing. FIG. 6B shows that K562 overexpressing CD47 (see FIG. 1A for CD47 expression levels) were less susceptible to primary NK cell killing and the killing was much more inefficient. Blocking SIRPα improved the killing capacity of primary NK cells against CD47-overexpressing K562 (mean±s.d., 3 independent experiments per group).

FIGS. 7A to 7C show how different CD47 levels affect human cancer cell line killing. In the upper panels, flow cytometry data of CD47 expression versus isotype control are shown. Results were expressed as mean fluorescent intensity fold-change to isotype-matched control Ig staining. The cancer cell lines Hutu80 (FIG. 7A, upper panel) and NCCIT (FIG. 7B, upper panel) showed low levels of surface CD47 expression. Detroit 562, however, showed very high CD47 expression (FIG. 7C, upper panel). In FIG. 7A and FIG. 7B (lower panels), IL-2-stimulated NK cells showed efficient cancer cell killing that was not affected by a CD47 blocking antibody. Thus, CD47 did not have any protective effects on these cell lines. In FIG. 7C (lower panel), however, CD47 blocking significantly increased the NK cell killing of the Detroit 562 line with high CD47.

Figure 8A:
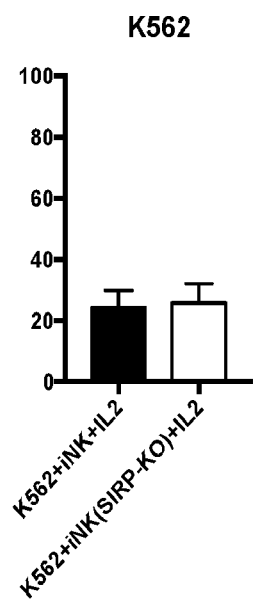
Figure 8B:
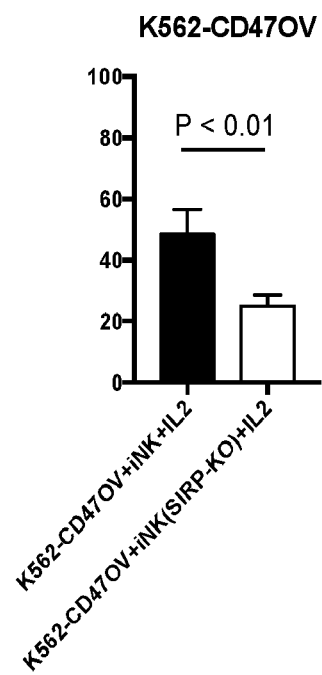

FIGS. 8A and 8B show that HIP iPSC-derived NK cells kill CD47+ cancer cells. Human HIP iPSCs (B2M–/–CIITA –/–CD47tg) underwent additional gene editing to knock out the SIRPα genes. These SIRPA –/–iPSCs were then differentiated into NK cells (iNK (SIRP-KO)). iNK cells derived from human HIP iPSCs served as controls. Killing of firefly luciferase-expressing K562 lines was assessed by bioluminescence imaging and the photon emmission was assessed. When K562 were used as target cells, both iNKs and iNK (SIRP-KO) showed similar killing efficacy (FIG. 8A). When K562 targets overexpressing CD47 were used, the iNK (SIRP-KO) were more aggressive, while iNKs showed some reduced killing capacity (FIG. 8B).

VI. DETAILED DESCRIPTION OF THE INVENTION

A. Introduction

SIRPα signal regulatory protein alpha is a member of the signal-regulatory-protein (SIRP) family and also belongs to the immunoglobulin superfamily. SIRP family members are receptor-type transmembrane glycoproteins known to be involved in the negative regulation of receptor tyrosine kinase-coupled signaling processes. SIRPα can be phosphorylated by tyrosine kinases. The phosphotyrosine residues recruit SH2 domain-containing tyrosine phosphatases (PTP) and serve as their substrates. SIRPα participates in signal transduction mediated by various growth factor receptors.

CD47 is a ligand for SIRPα. CD47 is a "marker-of-self" protein that can be overexpressed broadly across tumor types. It is emerging as a novel potent macrophage immune checkpoint for cancer immunotherapy. CD47 in tumor cells sends a "don't-eat-me" signal that inhibits macrophage phagocytosis. It presents opportunities and challenges for CD47 inhibitors both as a monotherapy and in combination treatments for hematological cancers and solid tumors. Some of these agents are currently in clinical trials.

Previously, the art has not recognized that NK cells express SIRPα. This is likely because established NK cell lines do not express SIRPα and primary NK cells express SIRPα only after stimulation with cytokines like IL2 or IL15. NK cells do not kill certain solid or hematologic tumors efficiently. The invention recognizes for the first time that human primary NK cells express SIRPα upon stimulation and bind to CD47. This reduces their killing efficacy for all kinds of CD47-expressing tumors. Thus, the invention provides, for the first time, NK cells that are more effective for killing previously less susceptible solid and hematologic tumors because they have reduced or ablated SIRPα-expression.

B. Definitions

As used herein, the terms "subject" or "patient" refers to any animal, such as a domesticated animal, a zoo animal, or a human. The "subject" or "patient" can be a mammal like a dog, cat, bird, livestock, or a human. Specific examples of "subjects" and "patients" include, but are not limited to, individuals (particularly human) with a disease or disorder related to the liver, heart, lung, kidney, pancreas, brain, neural tissue, blood, bone, bone marrow, and the like.

Mammalian cells can be from humans or non-human mammals. Exemplary non-human mammals include, but are not limited to, mice, rats, cats, dogs, rabbits, guinea pigs, hamsters, sheep, pigs, horses, bovines, and non-human primates (e.g., chimpanzees, macaques, and apes).

By "hypo-immunogenic" cell or "HI" cell herein is meant a cell that gives rise to a reduced immunological rejection response when transferred into an allogeneic host. In preferred embodiments, HI cells do not give rise to an immune response. Thus, "hypo-immunogenic" refers to a significantly reduced or eliminated immune response when compared to the immune response of a parental (i.e. "wt") cell prior to immunoengineering.

By "hypo-immunogenic cell O−" "hypo-immunogenic ORh−" cell or "HIO-" cell herein is meant a HI cell that is also ABO blood group O and Rhesus Factor Rh-. HIO- cells may have been generated from O− cells, enzymatically modified to be O−, or genetically engineered to be O−.

By "HLA" or "human leukocyte antigen" complex is a gene complex encoding the major histocompatibility complex (MHC) proteins in humans. These cell-surface proteins that make up the HLA complex are responsible for the regulation of the immune response to antigens. In humans, there are two MHCs, class I and class II, "HLA-I" and "HLA-II". HLA-I includes three proteins, HLA-A, HLA-B and HLA-C, which present peptides from the inside of the cell, and antigens presented by the HLA-I complex attract killer T-cells (also known as CD8+ T-cells or cytotoxic T cells). The HLA-I proteins are associated with β-2 microglobulin (B2M). HLA-II includes five proteins, HLA-DP, HLA-DM, HLA-DOB, HLA-DQ and HLA-DR, which present antigens from outside the cell to T lymphocytes. This stimulates CD4+ cells (also known as T-helper cells). It should be understood that the use of either "MHC" or "HLA" is not meant to be limiting, as it depends on whether the genes are from humans (HLA) or murine (MHC). Thus, as it relates to mammalian cells, these terms may be used interchangeably herein.

By "gene knock out" herein is meant a process that renders a particular gene inactive in the host cell in which it resides, resulting either in no protein of interest being produced or an inactive form. As will be appreciated by those in the art and further described below, this can be accomplished in a number of different ways, including removing nucleic acid sequences from a gene, or interrupting the sequence with other sequences, altering the reading frame, or altering the regulatory components of the nucleic acid. For example, all or part of a coding region of the gene of interest can be removed or replaced with "nonsense" sequences, all or part of a regulatory sequence such as a promoter can be removed or replaced, translation initiation sequences can be removed or replaced, etc.

By "gene knock in" herein is meant a process that adds a genetic function to a host cell. This causes increased levels of the encoded protein. As will be appreciated by those in the art, this can be accomplished in several ways, including adding one or more additional copies of the gene to the host cell or altering a regulatory component of the endogenous gene increasing expression of the protein is made. This may be accomplished by modifying the promoter, adding a different promoter, adding an enhancer, or modifying other gene expression sequences. "β-2 microglobulin" or "β2M" or "B2M" protein refers to the human β2M protein that has the amino acid and nucleic acid sequences shown below; the human gene has accession number NC_000015.10: 44711487-44718159.

"CD47 protein" protein refers to the human CD47 protein that has the amino acid and nucleic acid sequences shown below; the human gene has accession number NC_000016.10:10866208-10941562.

"CIITA protein" protein refers to the human CIITA protein that has the amino acid and nucleic acid sequences shown below; the human gene has accession number NC_000003.12:108043094-108094200.

By "wild type" in the context of a cell means a cell found in nature. However, in the context of a natural killer (NK) cell, as used herein, it also means that the cell may contain nucleic acid changes resulting in immortality but did not undergo the gene editing procedures of the invention to achieve hypo-immunogenicity.

By "syngeneic" herein refers to the genetic similarity or identity of a host organism and a cellular transplant where there is immunological compatibility; e.g. no immune response is generated.

By "allogeneic" herein refers to the genetic dissimilarity of a host organism and a cellular transplant where an immune response is generated.

By "B2M−/−" herein is meant that a diploid cell has had the B2M gene inactivated in both chromosomes. As described herein, this can be done in a variety of ways.

By "CIITA −/−" herein is meant that a diploid cell has had the CIITA gene inactivated in both chromosomes. As described herein, this can be done in a variety of ways.

By "CD47 tg" (standing for "transgene" or "CD47+") herein is meant that the host cell expresses CD47, in some cases by having at least one additional copy of the CD47 gene.

The term percent "identity," in the context of two or more nucleic acid or polypeptide sequences, refers to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

"Inhibitors," "activators," and "modulators" affect a function or expression of a biologically-relevant molecule. The term "modulator" includes both inhibitors and activators. They may be identified using in vitro and in vivo assays for expression or activity of a target molecule.

"Inhibitors" are agents that, e.g., inhibit expression or bind to target molecules or proteins. They may partially or totally block stimulation or have protease inhibitor activity. They may reduce, decrease, prevent, or delay activation, including inactivation, desensitizion, or down regulation of the activity of the described target protein. Modulators may be antagonists of the target molecule or protein.

"Activators" are agents that, e.g., induce or activate the function or expression of a target molecule or protein. They may bind to, stimulate, increase, open, activate, or facilitate the target molecule activity. Activators may be agonists of the target molecule or protein.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a specific embodiment, homologous or derivative sequences share at least an 80 or 85 percent sequence identity. In a specific embodiment, homologous or derivative sequences share at least a 90 percent sequence identity. In a specific embodiment, homologous or derivative sequences share at least a 95 percent sequence identity. In a more specific embodiment, homologous or derivative sequences share at least an 50, 55, 60, 65, 70, 75, 85, 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature that can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers (1995), incorporated by reference herein in its entirety.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficol1/0.1% polyvinylpyrrolidone/50 Mm sodium phosphate buffer at Ph 6.5 with 750 Mm sodium chloride, 75 Mm sodium citrate at 42° C.; or (3) overnight hybridization in a solution that employs 50% formamide, 5×SSC (0.75 M NaCl, 0.075 M sodium citrate), 50 Mm sodium phosphate (Ph 6.8), 0.1% sodium pyrophosphate, 5×Denhardt's solution, sonicated salmon sperm DNA (50 μl/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein the term "modification" refers to an alteration that physically differentiates the modified molecule from the parent molecule. In one embodiment, an amino acid change in a SIRPα, CD47, HSVtk, EC-CD, or iCasp9 variant polypeptide prepared according to the methods described herein differentiates it from the corresponding parent that has not been modified according to the methods described herein, such as wild-type proteins, a naturally occurring mutant proteins or another engineered protein that does not include the modifications of such variant polypeptide. In another embodiment, a variant polypeptide includes one or more modifications that differentiates the function of the variant polypeptide from the unmodified polypeptide. For example, an amino acid change in a variant polypeptide affects its receptor binding profile. In other embodiments, a variant polypeptide comprises substitution, deletion, or insertion modifications, or combinations thereof. In another embodiment, a variant polypeptide includes one or more modifications that increases its affinity for a receptor compared to the affinity of the unmodified polypeptide.

In one embodiment, a variant polypeptide includes one or more substitutions, insertions, or deletions relative to a corresponding native or parent sequence. In certain embodiments, a variant polypeptide includes 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31-40, 41 to 50, or 51 or more modifications.

By "episomal vector" herein is meant a genetic vector that can exist and replicate autonomously in the cytoplasm of a cell; e.g. it is not integrated into the genomic DNA of the host cell. A number of episomal vectors are known in the art and described below.

By "knock out" in the context of a gene means that the host cell harboring the knock out does not produce a functional protein product of the gene. As outlined herein, a knock out can result in a variety of ways, from removing all or part of the coding sequence, introducing frameshift mutations such that a functional protein is not produced (either truncated or nonsense sequence), removing or altering a regulatory component (e.g. a promoter) such that the gene is not transcribed, preventing translation through binding to mRNA, etc. Generally, the knock out is effected at the genomic DNA level, such that the cells' offspring also carry the knock out permanently.

By "knock in" in the context of a gene means that the host cell harboring the knock in has more functional protein active in the cell. As outlined herein, a knock in can be done in a variety of ways, usually by the introduction of at least one copy of a transgene (tg) encoding the protein into the cell, although this can also be done by replacing regulatory components as well, for example by adding a constitutive promoter to the endogeneous gene. In general, knock in technologies result in the integration of the extra copy of the transgene into the host cell.

VII. CELLS OF THE INVENTION

The invention provides compositions and methodologies for generating a SIRPα– NK cell. In some embodiments, the cells are HIO-SIRPα– NK cells.

A. Methodologies for Genetic Alterations

The invention includes methods of modifying nucleic acid sequences within cells or in cell-free conditions to generate SIRPα– NK cells. Exemplary technologies include homologous recombination, knock-in, ZFNs (zinc finger nucleases), TALENs (transcription activator-like effector nucleases), CRISPR (clustered regularly interspaced short palindromic repeats)/Cas9, and other site-specific nuclease technologies. These techniques enable double-strand DNA breaks at desired locus sites. These controlled double-strand breaks promote homologous recombination at the specific locus sites. This process focuses on targeting specific sequences of nucleic acid molecules, such as chromosomes, with endonucleases that recognize and bind to the sequences and induce a double-stranded break in the nucleic acid molecule. The double-strand break is repaired either by an error-prone non-homologous end-joining (NHEJ) or by homologous recombination (HR).

As will be appreciated by those in the art, a number of different techniques can be used to engineer the NK cells of the invention, as well as the engineering them to become hypo-immunogenic as outlined herein.

In general, these techniques can be used individually or in combination. For example, in the generation of the SIRPα–NK cells, CRISPR may be used to reduce the expression of active SIRPα protein in the engineered cells. In another example, viral techniques (e.g. lentivirus) are used to knock in genes such as CD47.

a. CRISPR Technologies

In one embodiment, the cells are manipulated using clustered regularly interspaced short palindromic repeats)/Cas ("CRISPR") technologies as is known in the art. CRISPR can be used to generate the SIRPα– NK cells. There are a large number of techniques based on CRISPR, see for example Doudna and Charpentier, Science doi: 10.1126/science.1258096, hereby incorporated by reference. CRISPR techniques and kits are sold commercially.

b. TALEN Technologies

In some embodiments, the cells of the invention are made using Transcription Activator-Like Effector Nucleases (TALEN) methodologies. TALEN are restriction enzymes combined with a nuclease that can be engineered to bind to and cut practically any desired DNA sequence. TALEN kits are sold commercially.

c. Zinc Finger Technologies

In one embodiment, the cells are manipulated using Zn finger nuclease technologies. Zn finger nucleases are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms, similar to CRISPR and TALENs.

d. Viral Based Technologies

There are a wide variety of viral techniques that can be used to generate some embodiments of the SIRPα– NK cells of the invention including, but not limited to, the use of retroviral vectors, lentiviral vectors, adenovirus vectors and Sendai viral vectors. Episomal vectors used in the generation of the cells are described below.

e. Down Regulation of Genes Using Interfering RNA

In other embodiments, genes that encode proteins used in HLA molecules are downregulated by RNAi technologies. RNA interference (RNAi) is a process where RNA molecules inhibit gene expression often by causing specific mRNA molecules to degrade. Two types of RNA molecules—microRNA (miRNA) and small interfering RNA (siRNA)—are central to RNA interference. They bind to the target mRNA molecules and either increase or decrease their activity. RNAi helps cells defend against parasitic nucleic acids such as those from viruses and transposons. RNAi also influences development.

siRNA. Small interfering RNAs are double-stranded RNA fragments that may be 21-22 nucleotides long. The first step to employing siRNAs in therapeutic applications is designing an siRNA sequence that is specific to the target mRNA using multiple algorithms that are known in the art. The siRNAs are produced by chemical synthesis or through gene expression. Once siRNA enters a cell, the process of gene silencing is initiated and carried out by the endogenous RNAi pathway. The antisense strand is loaded into a protein complex called the RNA-induced silencing complex (RISC). It serves as a guide for recognizing complementary mRNAs. After the target sequence is recognized, the mRNA is cleaved between 10 and 11 nucleotides downstream from the 5' end of the antisense strand by Argonaute 2, a component of the RISC. This results in reduced protein expression from the silenced gene. Advantages of siRNAs over drug therapies include their high degree of specificity and low toxicity. See Ahmadzada et al, *Biophys Rev.* 10(1):69-86 (2018), incorporated herein by reference in its entirety.

ASO. Antisense oligonucleotides are short, synthetic, single-stranded oligodeoxynucleotides that can alter RNA and reduce, restore, or modify protein expression through several distinct mechanisms. First generation ASOs were short, synthetic, single stranded oligodeoxynucleotides, typically 8-50 nucleotides in length. They are bound by complementary base pairing to a target mRNA. This causes endonuclease-mediated RNA transcript knockdown, and thus, reduced levels of the encoded target protein. Second and third generation ASOs with modified backbones confer enhanced pharmacological properties. These improved ASOs can function via alternative mechanisms. For example, they can alter pre-mRNA splicing by sterically blocking splicing factors or they can block mRNA translation by preventing ribosome recruitment. See Rinaldi and Wood, *Nat. Rev. Neurol.* 14(1):9-21 2018, incorporated by reference herein in its entirety.

Some ASOs use a phosphorothioate backbone. One of the nonbridging oxygen atoms of the ASO backbone is replaced with a sulfur which substantially improves resistance to nuclease activity and increases binding to serum proteins. These alterations increased the half-lives of ASOs in serum while still enabling the molecules to be used in applications that involved downregulation of target RNA. In addition, modifications at the 2' position of the ribose sugar have yielded another class of ASOs with improved safety and efficacy profiles, including 2'O-methyl (2'OMe), 2'Omethoxyethyl (2'MOE) oligonucleotides, and Locked Nucleic Acids (LNAs).

LNA: To enhance the in vivo activity of ASOs, many artificial nucleic acids have been synthesized to improve nuclease resistance, binding properties, RNase H activity, and serum stability. Locked nucleic acids (also known as 2'-O,4'-C-methylene-bridged nucleic acid (2',4'-BNA) are artificial nucleic acid derivatives that contain a methylene bridge connecting the 2'-O with the 4'-C position in the furanose ring. This enables them to form a strictly N-type conformation that offers high binding affinity against complementary RNA. LNA also presents enzyme resistance, similar to other nucleic acid derivatives. LNAs are used for various gene silencing techniques, such as antisense, short interfering RNA, blocking of microRNA, and triplex-forming oligonucleotides. LNAs can be used, for example, in Splice Switching Oligonucleotides (SSOs) and LNA-based SSOs (LNA SSOs) are functional in vivo in mouse models See Shimo et. Al. *Nucleic Acids Research,* 42(12): 8174-8187 (2014), incorporated by reference herein in its entirety.

Gapmer ASOs are short single-stranded ASOs containing a central DNA sequence commonly flanked by a locked nucleic acid (LNA) sequence that interrupts mRNA expression by induction of RNase H activation. They can exhibit cellular entry without the necessity of a transfection agent by a process termed gymnosis.

SSO. Oligonucleotide-induced modulation of splicing leads to several outcomes in cell culture and in vivo that have potential therapeutic value. Splice-switching oligonucleotides (SSOs) are oligonucleotides that modulate pre-mRNA splicing, can repair defective RNA, and restore the production of essential proteins. They can also generate novel proteins with desirable properties and regulate the presence of disease-related splice variant proteins. The latter outcome is achieved by modulating alternative splicing of pre-mRNA.

To modulate pre-mRNA splicing, SSOs block RNA sequences that are essential for splicing and prevent the interaction of splicing factors—such as RNA-binding proteins, small nuclear RNAs and other components of the spliceosome—with the pre-mRNA. The chemistries that have been shown to work in animal models include peptide nucleic acids (PNAs), alternating locked nucleic acids (LNAs), deoxynucleotide oligonucleotides, fully modified (non-gapmer) 2'-substituted oligonucleotides, and PMO-based oligomers.

sdRNA. The sno-derived RNA molecules are a class of asymmetric siRNAs comprising a guide (antisense) strand of 19-21 bases. They contain a 5' phosphate, 2'Ome or 2'F modified pyrimidines, and six phosphotioates at the 3' positions. They also contain a sense strand containing 3' conjugated sterol moieties, 2 phospotioates at the 3' position, and 2'Ome modified pyrimidines. Both strands contain 2' Ome purines with continuous stretches of unmodified purines not exceeding a length of 3. sdRNA is disclosed in U.S. Pat. No. 8,796,443, incorporated by reference herein in its entirety.

For all of these technologies, well known recombinant techniques are used, to generate recombinant nucleic acids as outlined herein. In certain embodiments, the recombinant nucleic acids (either than encode a desired polypeptide, e.g. CD47, or disruption sequences) may be operably linked to one or more regulatory nucleotide sequences in an expression construct. Regulatory nucleotide sequences will generally be appropriate for the host cell and subject to be treated. Numerous types of appropriate expression vectors and suitable regulatory sequences are known in the art for a variety of host cells. Typically, the one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are also contemplated. The promoters may be either naturally occurring promoters, or hybrid promoters that combine elements of more than one promoter. An expression construct may be present in a cell on an episome, such as a plasmid, or the expression construct may be inserted in a chromosome. In a specific embodiment, the expression vector includes a selectable marker gene to allow the selection of transformed host cells. Certain embodiments include an expression vector comprising a nucleotide sequence encoding a variant polypeptide operably linked to at least one regulatory sequence. Regulatory sequence for use herein include promoters, enhancers, and other expression control elements. In certain embodiments, an expression vector is designed for the choice of the host cell to be transformed, the particular variant polypeptide desired to be expressed, the vector's copy number, the ability to control that copy number, or the expression of any other protein encoded by the vector, such as antibiotic markers.

Examples of suitable mammalian promoters include, for example, promoters from the following genes: ubiquitin/S27a promoter of the hamster (WO 97/15664), Simian vacuolating virus 40 (SV40) early promoter, adenovirus major late promoter, mouse metallothionein-I promoter, the long terminal repeat region of Rous Sarcoma Virus (RSV), mouse mammary tumor virus promoter (MMTV), Moloney murine leukemia virus Long Terminal repeat region, and the early promoter of human Cytomegalovirus (CMV). Examples of other heterologous mammalian promoters are the actin, immunoglobulin or heat shock promoter(s).

In additional embodiments, promoters for use in mammalian host cells can be obtained from the genomes of viruses such as polyoma virus, fowlpox virus (UK 2,211,504 published 5 Jul. 1989), bovine papilloma virus, avian sarcoma virus, cytomegalovirus, a retrovirus, hepatitis-B virus and Simian Virus 40 (SV40). In further embodiments, heterologous mammalian promoters are used. Examples include the actin promoter, an immunoglobulin promoter, and heat-shock promoters. The early and late promoters of SV40 are conveniently obtained as an SV40 restriction fragment which also contains the SV40 viral origin of replication. Fiers et al., Nature 273: 113-120 (1978). The immediate early promoter of the human cytomegalovirus is conveniently obtained as a HindIII E restriction fragment. Greenaway, P. J. et al., Gene 18: 355-360 (1982). The foregoing references are incorporated by reference in their entirety.

In some embodiments, the SIRPα– NK cells are derived from stem cells.

The term "pluripotent cells" refers to cells that can self-renew and proliferate while remaining in an undifferentiated state and that can, under the proper conditions, be induced to differentiate into specialized cell types. The term "pluripotent cells," as used herein, encompass embryonic stem cells (ESC) and other types of stem cells, including fetal, amnionic, or somatic stem cells. Exemplary human stem cell lines include the H9 human embryonic stem cell line. Additional exemplary stem cell lines include those made available through the National Institutes of Health Human Embryonic Stem Cell Registry and the Howard Hughes Medical Institute HUES collection (as described in Cowan, C. A. et. al, New England J. Med. 350:13. (2004), incorporated by reference herein in its entirety.)

"Pluripotent stem cells" as used herein have the potential to differentiate into any of the three germ layers: endoderm (e.g. the stomach linking, gastrointestinal tract, lungs, etc), mesoderm (e.g. muscle, bone, blood, urogenital tissue, etc) or ectoderm (e.g. epidermal tissues and nervous system tissues). The term "pluripotent stem cells," as used herein, also encompasses "induced pluripotent stem cells", or "iPSCs", a type of pluripotent stem cell derived from a non-pluripotent cell. Examples of parent cells include somatic cells that have been reprogrammed to induce a pluripotent, undifferentiated phenotype by various means. Such "iPS" or "iPSC" cells can be created by inducing the expression of certain regulatory genes or by the exogenous application of certain proteins. Methods for the induction of iPS cells are known in the art and are further described below. (See, e.g., Zhou et al., Stem Cells 27 (11): 2667-74 (2009); Huangfu et al., Nature Biotechnol. 26 (7): 795 (2008); Woltjen et al., Nature 458 (7239): 766-770 (2009); and Zhou et al., Cell Stem Cell 8:381-384 (2009); each of which is incorporated by reference herein in their entirety.) The generation of induced pluripotent stem cells (iPSCs) is outlined below. As used herein, "hiPSCs" are human induced pluripotent stem cells, and "miPSCs" are murine induced pluripotent stem cells.

"Pluripotent stem cell characteristics" refer to characteristics of a cell that distinguish pluripotent stem cells from other cells. The ability to give rise to progeny that can undergo differentiation, under the appropriate conditions, into cell types that collectively demonstrate characteristics associated with cell lineages from all of the three germinal layers (endoderm, mesoderm, and ectoderm) is a pluripotent stem cell characteristic. Expression or non-expression of certain combinations of molecular markers are also pluripotent stem cell characteristics. For example, human pluripotent stem cells express at least several, and in some embodiments, all of the markers from the following non-limiting list: S SEA-3, SSEA-4, TRA-1-60, TRA-1-81, TRA-2-49/6E, ALP, Sox2, E-cadherin, UTF-1, Oct4, Rex1, and Nanog. Cell morphologies associated with pluripotent stem cells are also pluripotent stem cell characteristics. As described herein, cells do not need to pass through pluripotency to be reprogrammed into endodermal progenitor cells and/or hepatocytes.

B. Generation of Hypo-Immunogenic (HI) SIRPα– NK Cells

Generating HI cells is done with as few as three genetic changes, resulting in minimal disruption of cellular activity but conferring immunosilencing to the cells. The techniques are disclosed in, e.g., Int'l App. No. WO2018132783, incorporated by reference herein in its entirety. The techniques are discussed briefly below.

As discussed herein, one embodiment utilizes a reduction or elimination in the protein activity of MHC I and II (HLA I and II when the cells are human). This can be done by altering genes encoding their components. In one embodiment, the coding region or regulatory sequences of the gene are disrupted using CRISPR. In another embodiment, gene translation is reduced using interfering RNA technologies. Another embodiment is a change in a gene that regulates susceptibility to macrophage phagocytosis, such as CD47, and this is generally a "knock in" of a gene using viral technologies.

1. HLA-I Reduction

The HI SIRPα– NK cells of the invention include a reduction in MHC I function (HLA I when the cells are derived from human cells).

As will be appreciated by those in the art, the reduction in function can be accomplished in a number of ways, including removing nucleic acid sequences from a gene, interrupting the sequence with other sequences, or altering the regulatory components of the nucleic acid. For example, all or part of a coding region of the gene of interest can be removed or replaced with "nonsense" sequences, frameshift mutations can be made, all or part of a regulatory sequence such as a promoter can be removed or replaced, translation initiation sequences can be removed or replaced, etc.

As will be appreciated by those in the art, the successful reduction of the MHC I function (HLA I when the cells are derived from human cells) in the SIRPα– NK cells can be measured using techniques known in the art and as described below; for example, FACS techniques using labeled antibodies that bind the HLA complex; for example, using commercially available HLA-A,B,C antibodies that bind to the alpha chain of the human major histocompatibility HLA Class I antigens.

a. B2M Alteration

In one embodiment, the reduction in HLA-I activity is done by disrupting the expression of the β-2 microglobulin gene in the HI SIRPα– NK cell, the human sequence of which is disclosed herein. This alteration is generally referred to herein as a gene "knock out", and in the cells of the invention it is done on both alleles in the host cell. Generally the techniques to do both disruptions is the same.

A particularly useful embodiment uses CRISPR technology to disrupt the gene. In some cases, CRISPR technology is used to introduce small deletions/insertions into the coding region of the gene, such that no functional protein is produced, often the result of frameshift mutations that result in the generation of stop codons such that truncated, non-functional proteins are made.

Accordingly, a useful technique is to use CRISPR sequences designed to target the coding sequence of the B2M gene in mouse or the B2M gene in human. After gene editing, the transfected SIRPα– NK cultures are dissociated to single cells. Single cells are expanded to full-size colonies and tested for CRISPR edit by screening for presence of aberrant sequence from the CRISPR cleavage site. Clones with deletions in both alleles are picked. Such clones did not express B2M as demonstrated by PCR and did not express HLA-I as demonstrated by FACS analysis (see examples 1 and 6, for example).

Assays to test whether the B2M gene has been inactivated are known and described herein. In one embodiment, the assay is a Western blot of cells lysates probed with antibodies to the B2M protein. In another embodiment, reverse transcriptase polymerase chain reactions (rt-PCR) confirms the presence of the inactivating alteration.

In addition, the cells can be tested to confirm that the HLA I complex is not expressed on the cell surface. This may be assayed by FACS analysis using antibodies to one or more HLA cell surface components as discussed above.

2. HLA-II Reduction

In some embodiments, in addition to a reduction in HLA I, the HI SIRPα– NK cells of the invention may also lack MHC II function (HLA II from human-derived cells).

As will be appreciated by those in the art, the reduction in function can be accomplished in a number of ways, including removing nucleic acid sequences from a gene, adding nucleic acid sequences to a gene, disrupting the reading frame, interrupting the sequence with other sequences, or altering the regulatory components of the nucleic acid. In one embodiment, all or part of a coding region of the gene of interest can be removed or replaced with "nonsense" sequences. In another embodiment, regulatory sequences such as a promoter can be removed or replaced, translation initiation sequences can be removed or replaced, etc.

The successful reduction of the MHC II (HLA II) function in the SIRPα– NK cells or their derivatives can be measured using techniques known in the art such as Western blotting using antibodies to the protein, FACS techniques, rt-PCR techniques, etc.

a. CIITA Alteration

In one embodiment, the reduction in HLA-II activity is done by disrupting the expression of the CIITA gene in the SIRPα– NK cell, the human sequence of which is shown herein. This alteration is generally referred to herein as a gene "knock out", and in the SIRPα– NK cells of the invention it is done on both alleles in the host cell.

Assays to test whether the CIITA gene has been inactivated are known and described herein. In one embodiment, the assay is a Western blot of cells lysates probed with antibodies to the CIITA protein. In another embodiment, reverse transcriptase polymerase chain reactions (rt-PCR) confirms the presence of the inactivating alteration.

In addition, the cells can be tested to confirm that the HLA II complex is not expressed on the cell surface. Again, this assay is done as is known in the art. Exemplary analyses include Western Blots or FACS analysis using commercial antibodies that bind to human HLA Class II HLA-DR, DP and most DQ antigens as outlined below.

A particularly useful embodiment uses CRISPR technology to disrupt the CIITA gene. CRISPRs ae designed to target the coding sequence of the CIITA gene, an essential transcription factor for all MHC II molecules. After gene editing, the transfected cell cultures are dissociated into single cells. They are expanded to full-size colonies and tested for successful CRISPR editing by screening for the presence of an aberrant sequence from the CRISPR cleavage site. Clones with deletions that do not express CIITA are determined by PCR and may be shown not to express MHC II/HLA-II by FACS analysis.

3. Phagocytosis Reduction

In addition to the reduction of HLA I and II (or MHC I and II), generally using B2M and CIITA knock-outs, the HI SIRPα– NK cells of the invention have a reduced susceptibility to macrophage phagocytosis and NK cell killing. The resulting cells "escape" the immune macrophage and innate pathways due to one or more CD47 transgenes.

a. CD47 Increase

In some embodiments, reduced macrophage phagocytosis and NK cell killing susceptibility results from increased CD47 on the HI SIRPα– NK cell surface. This is done in several ways as will be appreciated by those in the art using "knock in" or transgenic technologies. In some cases, increased CD47 expression results from one or more CD47 transgenes.

Accordingly, in some embodiments, one or more copies of a CD47 gene is added to the SIRPα– NK cells under the control of an inducible or constitutive promoter, with the latter being preferred. In some embodiments, a lentiviral construct is employed as described herein or known in the art. CD47 genes may integrate into the genome of the host cell under the control of a suitable promoter as is known in the art.

In some embodiments, the expression of the CD47 gene can be increased by altering the regulatory sequences of the endogenous CD47 gene, for example, by exchanging the endogenous promoter for a constitutive promoter or for a different inducible promoter. This can generally be done using known techniques such as CRISPR.

Once altered, the presence of sufficient CD47 expression can be assayed using known techniques such as those described in the Examples, such as Western blots, ELISA assays or FACS assays using anti-CD47 antibodies. In general, "sufficiency" in this context means an increase in the expression of CD47 on the HI SIRPα– NK cell surface that silences NK cell killing. The natural expression levels on cells is too low to protect them from NK cell lysis once their MHC I is removed.

4. Suicide Genes

In some embodiments, the invention provides HI SIRPα– NK cells that comprise a "suicide gene" or "suicide switch". These are incorporated to function as a "safety switch" that can cause the death of the cells should they grow and divide in an undesired manner. The "suicide gene" ablation approach includes a suicide gene in a gene transfer vector encoding a protein that results in cell killing only when activated by a specific compound. A suicide gene may encode an enzyme that selectively converts a nontoxic compound into highly toxic metabolites. The result is specifically eliminating cells expressing the enzyme. In some embodiments, the suicide gene is the herpesvirus thymidine kinase (HSV-tk) gene and the trigger is ganciclovir. In other embodiments, the suicide gene is the Escherichia coli cytosine deaminase (EC-CD) gene and the trigger is 5-fluorocytosine (5-FC) (Barese et al., *Mol. Therap.* 20(10):1932-1943 (2012), Xu et al., *Cell Res.* 8:73-8 (1998), both incorporated herein by reference in their entirety.)

In other embodiments, the suicide gene is an inducible Caspase protein. An inducible Caspase protein comprises at least a portion of a Caspase protein capable of inducing apoptosis. In preferred embodiments, the inducible Caspase protein is iCasp9. It comprises the sequence of the human FK506-binding protein, FKBP12, with an F36V mutation, connected through a series of amino acids to the gene encoding human caspase 9. FKBP12-F36V binds with high affinity to a small-molecule dimerizing agent, AP1903. Thus, the suicide function of iCasp9 in the instant invention is triggered by the administration of a chemical inducer of dimerization (CID). In some embodiments, the CID is the small molecule drug AP1903. Dimerization causes the rapid induction of apoptosis. (See WO2011146862; Stasi et al, *N. Engl. J. Med* 365; 18 (2011); Tey et al., *Biol. Blood Marrow Transplant.* 13:913-924 (2007), each of which are incorporated by reference herein in their entirety.)

5. Assays for HI Phenotypes

Once the HI cells have been generated, they may be assayed for their hypo-immunogenicity as is generally described herein.

For example, hypo-immunogenicity are assayed using a number of techniques One exemplary technique includes transplantation into allogeneic hosts and monitoring for HI SIRPα– NK cell survival. The cells may be transduced to express luciferase and can then followed using bioluminescence imaging. Similarly, the T cell or B cell response of the host animal to the HI SIRPα– NK cells are tested to confirm that they do not cause an immune reaction in the host animal. T cell function is assessed by Elispot, Elisa, FACS, PCR, or mass cytometry (CYTOF). B cell response or antibody response is assessed using FACS or luminex. Additionally, or alternatively, the cells may be assayed for their ability to avoid innate immune responses, e.g. NK cell killing. NK cell lytolytic activity is assessed in vitro or in vivo using techniques known in the art.

C. Generation of HI SIRPα– NK O– Cells

In some aspects of the invention, the HI SIRPα– NK cells generated as above will already be ABO blood group O and Rh factor negative (–) cells because the process will have started with NK cells having an O– blood type.

Other aspects of the invention involve the enzymatic conversion of A and B antigens. In preferred aspects, the B antigen is converted to O using an enzyme. In more preferred aspects, the enzyme is an α-galactosidase. This enzyme eliminates the terminal galactose residue of the B antigen. Other aspects of the invention involve the enzymatic conversion of A antigen to O. In preferred aspects, the A antigen is converted to O using an αN-acetylgalactosaminidase. Enzymatic conversion is discussed, e.g., in Olsson et al., *Transfusion Clinique et Biologique* 11:33-39 (2004); U.S. Pat. Nos. 4,427,777, 5,606,042, 5,633,130, 5,731,426, 6,184,017, 4,609,627, and 5,606,042; and Int'l Pub. No. WO9923210, each of which are incorporated by reference herein in their entirety.

Other embodiments of the invention involve genetically engineering the cells by knocking out the ABO gene Exon 7 or silencing the SLC14A1 (JK) gene. Other embodiments of the invention involve knocking out the C and E antigens of the Rh blood group system (RH), K in the Kell system (KEL), Fya and Fy3 in the Duffy system (FY), Jkb in the Kidd system (JK), or U and S in the MNS blood group system. Any knockout methodology known in the art or described herein, such as CRISPR, talens, or homologous recombination, may be employed.

Techniques for generating hypoimmune ABO blood group O h Factor (–) cells are described in Provisional App. No. 62/846,399 which is incorporated by reference herein in its entirety.

D. SIRPα– CAR-NK Cells

Chimeric antigen receptors (CARs, also known as chimeric immunoreceptors, chimeric T cell receptors or artificial T cell receptors) are receptor proteins that are engineered to give NK cells the new ability to target a specific protein. The receptors are chimeric because they combine both antigen-binding and T-cell activating functions into a single receptor.

CAR-NK cell therapy uses NK cells engineered with CARs for cancer therapy. The premise of CAR-NK immunotherapy is to modify NK cells to recognize cancer cells in order to more effectively target and destroy them. Human NK cells are expressing chimeric antigen receptors are transplanted into patients to attack their tumors. The CAR-NK cells can be either derived from NK cells in a patient's own blood (autologous) or derived from the NK cells of another healthy donor (allogeneic). Once isolated from a person, these NK cells are genetically engineered to express a specific CAR that programs them to target an antigen that is present on the surface of tumors. The CAR-NK cells of the invention can be made SIRPα– by any of the techniques disclosed herein.

E. Transplantation of HI SIRPα– NK Cells

As will be appreciated by those in the art that the HI SIRPα– NK cells are transplanted using techniques known in the art to reduce tumors and treat cancer. Exemplary cancers for treatment using the cells disclosed herein include acute myeloid leukemia, non-small cell lung cancer, urinary bladder neoplasms, hepatocellular carcinoma, melanoma, Merkel Cell carcinoma, triple negative breast cancer, ovarian cancer, renal cell carcinoma, colorectal cancer, and sarcoma.

In general, the HI SIRPα– NK cells of the invention are transplanted either intravenously or by injection at particular locations in the patient. When transplanted at particular locations, the cells may be suspended in a gel matrix to prevent dispersion while they take hold.

In order that the invention described herein may be more fully understood, the following examples are set forth. It should be understood that these examples are for illustrative purposes only and are not to be construed as limiting this invention in any manner.

VIII. EXAMPLES

Example 1

CD47 Expression Protects Cancer Cells from NK Cell-Mediated Killing

Cancer cells that express CD47 are protected from NK cell-mediated killing. K562 cells are a human, highly-malignant, immortalized myelogenous leukemia cell line. They were transfected to overexpress CD47 under a constitutive promoter with an approximately 6-fold increased expression levels (FIG. 1A).

Human K562 cells were a gift from Dr Lewis Lanier (UCSF, San Francisco, CA). The cells were cultured in RPMI 1640, 10% FCS hi and 1% Pen/Strep (all Gibco, Waltham, MA) as suspension cells. For transfections, $8\times10^3$ cells were plated per well into 48-well plates. Firefly-Luciferase virus particles (Gentarget, San Diego, CA) or human CD47 virus particles (Thermo Fisher, Waltham, CA) and 8 µg/mL polybrene (Sigma-Aldrich, St. Louis, MO) were added to the cell suspension and centrifuged down for 2 min at 1200 rpm. Plates were incubated at 37° C. in a cell incubator and the transfection was stopped after 48 h by media change. Successful transfection was confirmed by BLI for Firefly-Luciferase. Cells were incubated with 5 mg/mL D-Luciferin (Biosynth AG, Staad, Switzerland) for 10 min and the BLI signal was determinated on an amiHT bioimaging platform (Spectral Instruments Imaging, Tucson, AZ). For CD47 overexpression, cells were stained using an antibody against CD47 (clone MEM122, Thermo Fisher) or isotype-matched control Ig (mouse IgM, clone PFR-03, Thermo Fisher) and analyzed on FACS Calibur (BD Biosciences). Results were expressed as fold change untransduced K562.

FIG. 1B shows CD47-overexpressing K562 cultured with NK cells. K562 survival was measured by luciferase bioluminescence imaging (BLI) and the killing was quantified by a drop in BLI signal. CD47-overexpressing K562 were significantly protected from NK killing when compared to the K562 cells that do not overexpress CD47.

For K562 killing, assays were performed in 24 well plates using $5\times10^4$ K562 cells or $5\times10^4$ K562 CD47 as target cells, cocultured with $5\times10^4$ primary NK-cells as effector cells (ratio 1:1, StemCell Technologies, Vancouver, BC, Canada) in RPMI 1640, 10% FCS hi, 1% Pen/Strep, 1% MEMNEAA (all Gibco), 1% Natrium Pyruvat and 0.2% 2-Mercaptoethanol (both Millipore). NK-cells were prestimulated with human IL-2 overnight and during the assay (100 ng/mL, Peprotech). Plates were centrifuged down for 2 min at 1200 rpm. After 2 h incubation at 37° C., 5 mg/mL D-Luciferin (Biosynth AG) were added to the wells and BLI signals were quantified with Ami HT (Spectral Instruments Imaging) in maximum photons s −1 cm −2 per steradian per 24-well. Data were normalized against wells with target cells only. Some wells were pretreated with SIRPα blocking antibody (2 µg/mL, cat. no. MBS822365, MyBioSource, San Diego, CA) for 2 h and during the assay.

Example 2

SIRPα Interferes with NK Cell Killing when the Target Cells Express CD47

The invention recognizes for the first time that SIRPα is expressed on NK cells and that target cells expressing CD47 are more protected from NK cell killing. In particular, primary NK cells were shown to express SIRPα. SIRPα expression was examined on macrophages and primary NK cells using flow cytometry (LSR II, BD Biosciences). FIG. 2A shows SIRPα on macrophages, a known expressor (mean±s.d., 4 independent experiments per group). FIG. 2B shows that SIRPα was inducible with IL-2 on primary human NK cells (70036, Stemcell Technologies, Vancouver, Canada) and SIRPα progressively increased throughout the 5 day period. After 5 days, SIRPα on primary human NK cells was similar to SIRPα on macrophages.

PBMCs were isolated by Ficoll separation from fresh blood and were resuspend in RPMI-1640 with 10% heat-inactivated fetal calf sera (FCS hi), 1% pen/strep (all Gibco) and 10 ng/ml human M-CSF (Peprotech, Rocky Hill, NJ). Cells were plated in 24-well plates at a concentration of $1\times10^6$ cells per ml and medium was changed every second day. From day 6, 1 µg/ml human IL-2 (Peprotech) were added into the medium for 24 h before performing assays. Human primary NK cells were purchased from Stemcell Technologies and were cultured in RPMI-1640 plus 10% FCS hi, 1% pen/strep, 1% MEMNEAA, 1% Glutamine (all Gibco) before performing the assays. Cell culture was performed in T175 TC-treated, non-coated flasks (Corning) with a medium change every 2 days. The cells were sorted to be CD3− using anti-human CD3 MACS beads (Miltenyi, Auburn, CA) before the assays. Human primary NK cells were stimulated with IL2 100 ng/mL (Peprotech) for different time periods up to 5 days. Macrophages or NK cells were incubated with anti-SIRPα (clone: 15-414, Biolegend) and mouse IgG2a Isotype control (clone X39, BD Bioscience) for 45 min at 4° C. Results were expressed as mean fluorescent intensity fold-change to isotype-matched control Ig staining.

FIG. 2C shows that macrophages bind CD47. A chimera protein was used to establish CD47 binding. FIG. 2D shows that in parallel to the increasing SIRPα expression over 5 days shown in FIG. 2B, the binding of CD47 to primary human NK cells increased. Binding of the chimera protein was quantified using flow cytometry.

Macrophages were generated as described previously. Human primary NK cells were purchased from Stem Cell Technologies and cell culture was performed as described. NK cells were stimulated with human IL2 (100 ng/mL, Peprotech) for different time periods up to 5 days. Macrophages or NK cells were incubated with CD47 Chimera Protein (4670-CD, R&D systems) for 4 hours at 4° C. Human IgG1 antibody was used as secondary staining (polyclonal, Life Technologies) for 45 min at 4° C. Results were expressed as mean fluorescent intensity fold-change to control Ig staining with secondary antibody only.

NK cell lines require IL2 medium for continued culture. Thus, FIG. 3A shows SIRPα expression primary human NK cells and 4 established NK cell lines in IL2 medium. In contrast to primary human NK cells, which show SIRPα expression, the four established NK cell lines do not express SIRPα with IL2 stimulation. FIG. 3B shows that all 4 NK cell lines do not bind CD47. While primary NK cells interact with CD47, NK cell lines do not.

The lines NKL, NK-RL12 and NK-CT604 were cultured in RPMI-1640 containing 10% FCS-hi, 1% Pen/Strep, 1% L-Glutamine, 1% HEPES, 1% Sodium Pyruvate, 1% MEM-NEAA (all Gibco), 0.1% 2-mercaptoethanol (Millipore) and 100 ng/mL human IL-2 (Peprotech). The NK cell line NK-92 was cultured in alpha-MEM containing 10% FCS-hi, 10% horse serum hi, 1% Pen/Strep, 1% L-Glutamine (all Gibco), 0.2 mM Myo-Inositol, 0.02 mM Folic acid (both Sigma), 0.1% 2-mercaptoethanol (Millipore) and 100 ng/mL human IL-2 (Peprotech). Primary human NK cells were cultured as described above and also stimulated with 100 ng/mL human IL2. Cell culture was performed in T175 TC-treated, non-coated flasks with a medium change every second day. Flow cytometry for SIRPα expression and CD47 binding was performed as described above. The expression and binding was expressed as fold of the isotype control, thus a value of 1 equals no expression and no binding.

Many tumors down-regulate HLA class I and class II and upregulate CD47. This makes them "hypoimmune" and helps evade immune surveillance. An engineered B2M−/− CIITA −/−CD47 tg human induced endothelial cell (hiECs) was used as a hypoimmune tumor model because they don't express HLA class 1 and class 2 and they overexpress CD47.

A human episomal iPSC line derived from CD34+ cord blood using a three-plasmid, seven-factor (SOKMNLT; SOX2, OCT4 (POU5F1), KLF4, MYC, NANOG, LIN28, and SV40L T antigen) EBNA-based episomal system was used (Thermo Fisher Scientific, Waltham, MA). With CRISPR-Cas9 technology, the B2M and CIITA genes were disrupted to generate $B2M^{-/-}CIITA^{-/-}$ hiPSCs as described in Deuse T, et al. *Nat Biotechnol.* 2019 March; 37:252-258. To achieve CD47 overexpression, the CD47 cDNA was synthesized, cloned into a lentiviral plasmid, and cells were transfected to obtain a pool of $B2M^{-/-}CIITA^{-/-}$ CD47 tg hiPSC. Human iPSCs were cultured on diluted feeder-free matrigel (hESC qualified, BD Biosciences, San Jose, CA)-coated 10 cm dishes in Essential 8 Flex medium (Thermo Fisher Scientific). Medium was changed every 24 h and Versene (Gibco) was used for cell passaging at a ratio of 1:6. The differentiation to hiECs was started at 60% confluency, and medium was changed to RPMI-1640 containing 2% B-27 minus insulin (both Gibco) and 5 µM CHIR-99021 (Selleckchem). On day 2, the medium was changed to reduced medium: RPMI-1640 containing 2% B-27 minus insulin (Gibco) and 2 µM CHIR-99021 (Selleckchem). From day 4 to 7, cells were exposed to RPMI-1640 EC medium, RPMI-1640 containing 2% B-27 minus insulin plus 50 ng/ml human vascular endothelial growth factor (VEGF; R&D Systems), 10 ng/ml human fibroblast growth factor basic (FGFb; R&D Systems), 10 µM Y-27632 (Sigma-Aldrich), and 1 µM SB 431542 (Sigma-Aldrich). Endothelial cell clusters were visible from day 7 and cells were maintained in Endothelial Cell Basal Medium 2 (PromoCell, Heidelberg, Germany) plus supplements, 10% FCS hi (Gibco), 1% pen/strep, 25 ng/ml VEGF, 2 ng/ml FGFb, 10 µM Y-27632 (Sigma-Aldrich), and 1 µM SB 431542 (Sigma-Aldrich). The differentiation process was completed after 14 days and undifferentiated cells detached during the differentiation process. TrypLE Express (Gibco) was used for passaging the cells 1:3 every 3 to 4 days.

Figure 4C:
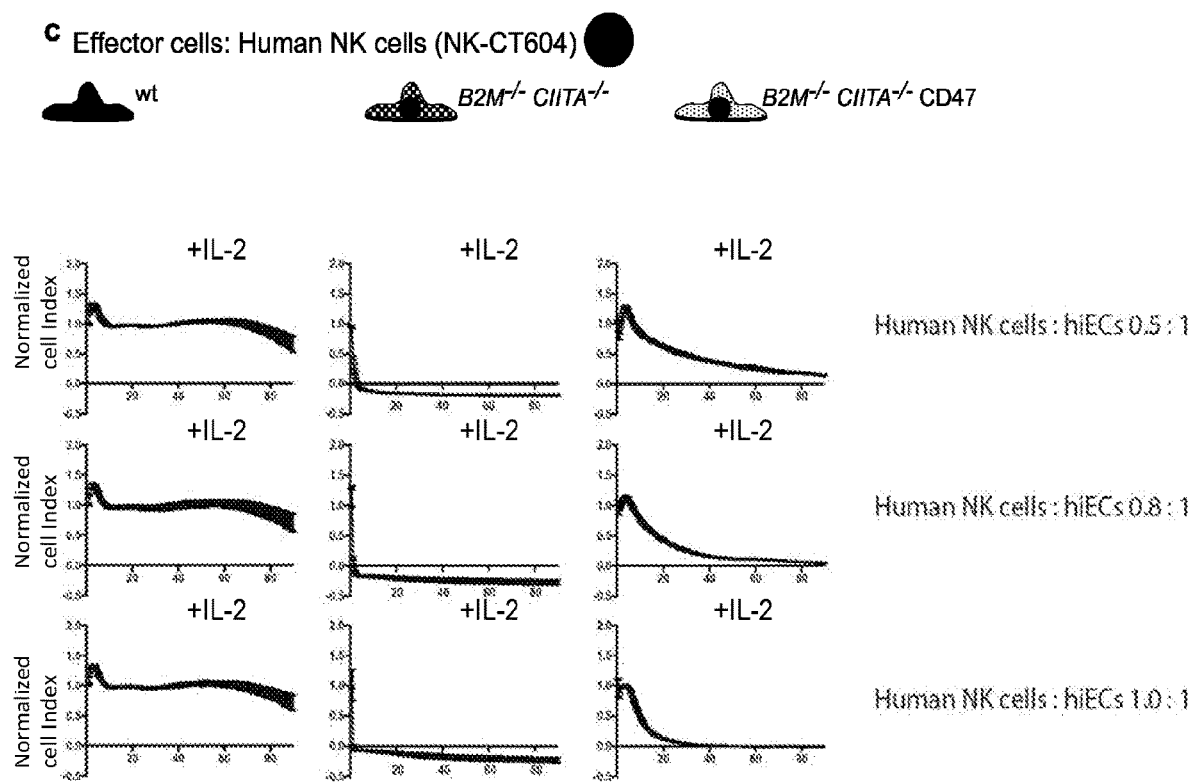
Figure 4D:
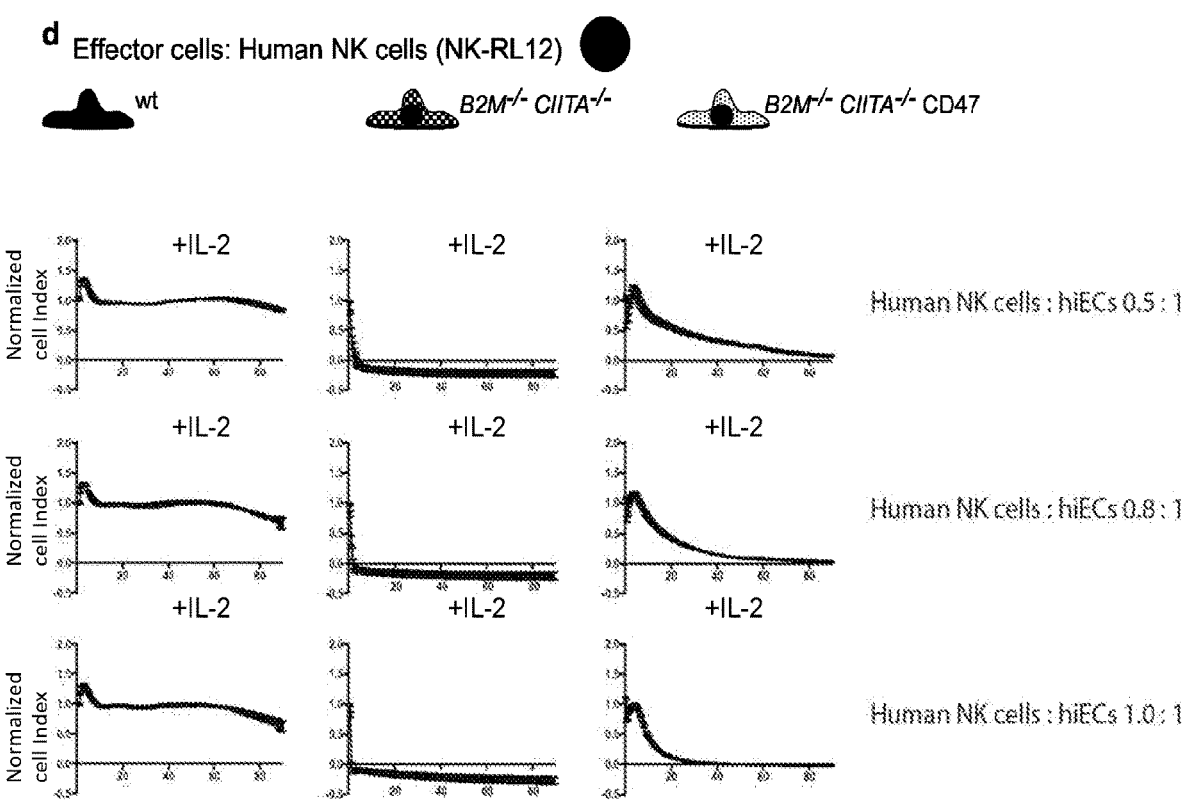
Figure 4E:
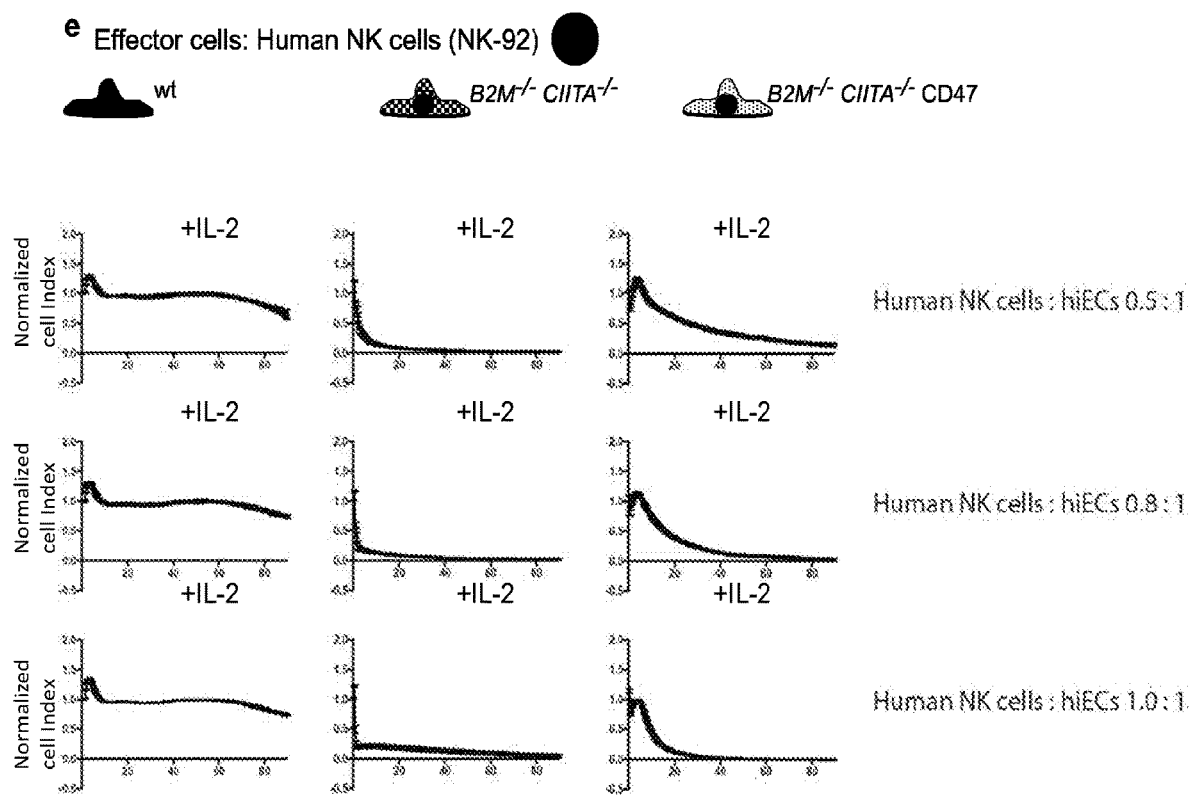

NK cell lines lacking SIRPα were more aggressive at killing B2M-/-CIITA -/-CD47 tg hiECs than primary NK cells expressing SIRPα. FIG. 4A shows that hiEC target cells lacking HLA class I and HLA class II (B2M-/-CIITA -/-) were quickly and efficiently killed by primary NK cells. Target cells, however, that additionally included CD47 overexpression were not killed. FIGS. 4B-4E showed the same pattern when the target cells lacked CD47. When the target cells overexpressed CD47, however, they died more rapidly then with the primary cells. FIG. 4B shows NKL cells. FIG. 4C shows NK-CT604 cells. FIG. 4D shows NK-RL12 cells. FIG. 4E shows NK-92 cells. The graphs show a mean±s.d., of three independent replicates per group and time points, three different effector cell: target cell (E:T) ratios.

NK cell killing assays were performed on the XCelligence SP platform and MP platform (ACEA BioSciences, San Diego, CA.). Special 96-well E-plates (ACEA BioSciences) were coated with collagen (Sigma-Aldrich) and $4\times10^5$ wt, $B2M^{-/-}CIITA^{-/-}$, or $B2M^{-/-}CIITA^{-/-}$CD47 tg (pooled or single clones) hiECs were plated in 100 µl cell-specific medium. After the cell index value reached 0.7, human NK cells were added at an E:T ratio of 0.5:1, 0.8:1, or 1:1 with 1 ng/ml human IL-2 (Peprotech).

Example 3

Blocking SIRPα on Primary NK Cells Increases Killing Efficiency

Figure 5D:
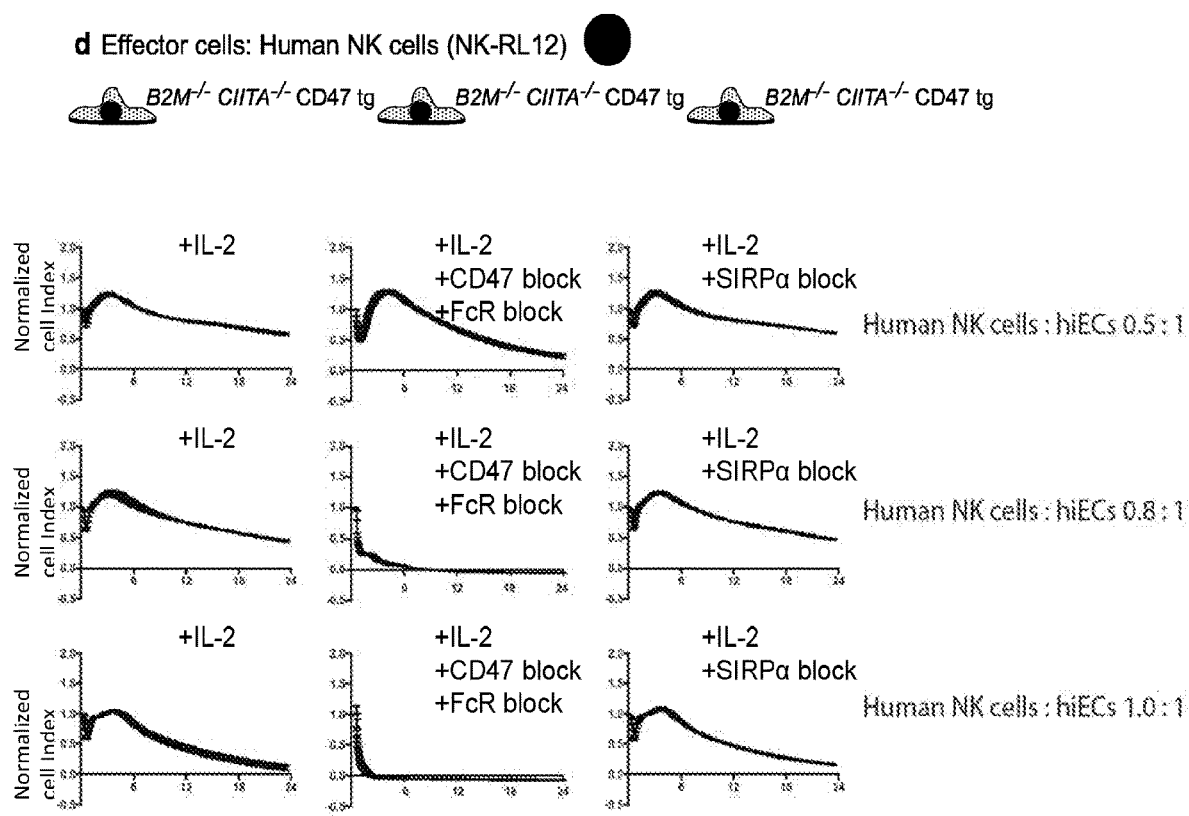
Figure 5E:
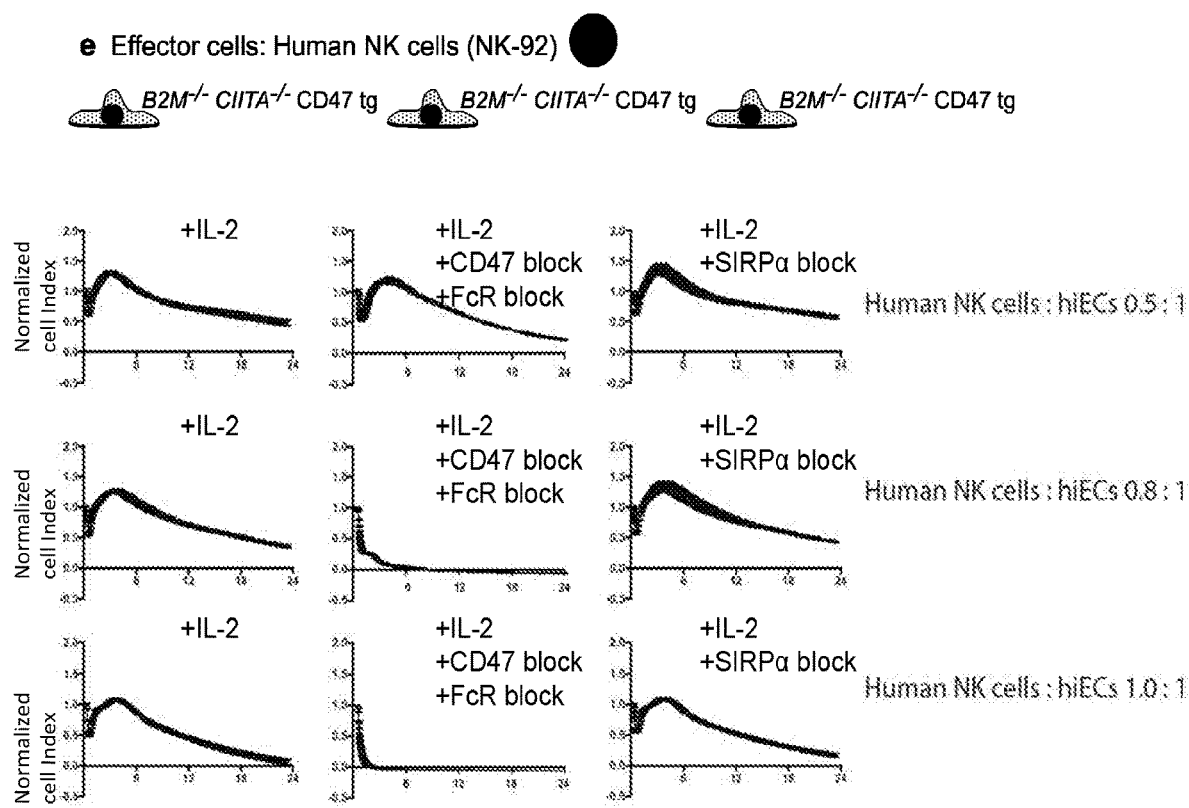

Blocking SIRPα on primary NK cells with an anti-SIRPα antibody greatly increased CD47+ cell killing against CD47 overexpressing target cells when compared with NK cell line killing. FIGS. 5A-5E shows killing curves of B2M-/-CIITA -/-CD47 tg hiECs from primary NK cell and NK cell line killing in the presence of IL2. In some experiments the CD47-SIRPα binding was prevented using specific antibodies against CD47 or SIRPα. FIG. 5A shows that primary NK cells very quickly killed the target cells if either CD47 or SIRPα was blocked. FIG. 5B shows the NKL cell line. FIG. 5C shows the NK-CT604 cell line. FIG. 5D shows the NK-RL12 cell line. FIG. 5E shows the NK-92 cell line. Together, neither blockade of CD47 nor SIRPα markedly changed the killing characteristic of the 4 NK cell lines. There was a mild trend towards faster killing with anti-CD47 in the NK cell lines, which may be an unspecific effect of either anti-CD47 or FcR block. This may facilitate antibody-mediated cellular cytotoxicity. The graphs show a mean±s.d., of three independent replicates per group and time points, three different E:T ratios.

NK cell killing assays were performed as described above. Some wells were pre-treated with anti-CD47 blocking antibody (10 µg/ml, clone B6.H12, BioXCell, West Lebanon, NH) for 2 h and during the assay, or with anti-SIRPα blocking blocking antibody (2 µg/ml, cat. no. MBS822365, MyBioSource) for 2 h and during the assay. In some cases, NK cells were pre-treated with human Fc receptor (FcR) block (cat. no. 130-059-901, Miltenyi) for 4 h before addition of target cells.

Antibodies blocked the interaction of target cell CD47 with primary NK cell SIRPα. Antibodies showed no clear effect on all 4 NK cell lines.

K562 and CD47-overexpressing K562 were transduced to express firefly luciferase. FIG. 6A shows that K562 are very effectively killed by primary NK cells in BLI assays if those are stimulated with IL2. Blocking of NK cell SIRPα did not enhance killing, suggesting that basal CD47 levels are not protecting K562 from NK cell killing. FIGS. 6B, however, shows that K562 overexpressing CD47 were less susceptible to primary NK cell killing and the killing was much more inefficient. IL2-stimulated pNK cells only killed approximately half of the K562 cancer cells, suggesting a survival benefit related to high levels of CD47. Blocking SIRPα improved the killing capacity of primary NK cells against CD47-overexpressing K562. SIRPα blocking made the cancer cells susceptible to NK killing and overturned the CD47 protection (mean±s.d., 3 independent experiments per group).

BLI killing assays were performed as described above.

The data show that the CD47-SIRPα immune checkpoint can be exploited by cancer cells to alleviate NK cell-based immune attack.

Example 4

Blocking CD47 on Cancer Cell Lines Increased Killing Efficiency

Different CD47 levels affect human cancer cell line killing. All cancer cells were transduced to express firefly luciferase and were expanded in culture. $1\times10^3$ cancer cells were grown as targets on a 96 well plate. Human primary NK cells underwent sorting for a CD3–CD7+CD56+ population and were then stimulated with human IL-2 for 3 days. The NK cells were then used as effector cells at a ratio of 10:1 to the target cells. In some experiments, human FcR blocking Ab and 10 µg/mL CD47 blocking Ab (BioXcell, Lebanon, NH, Cat #: BE0019-1) was incubated before the NK cells were added. After 120 minutes, luciferase expression was detected by adding D-luciferin. Triton X served as controls.

The cancer cell lines Hutu80 (FIG. 7A, upper panel) and NCCIT (FIG. 7B, upper panel) showed low levels of surface CD47 expression. Detroit 562, however, showed very high CD47 expression (FIG. 7C, upper panel). The expression was expressed as fold of the isotype control, thus a value of 1 equals no expression. A highly selected CD3−CD7+ CD56+ population of primary human NK cells was stimulated with IL-2 for 3 days. Then, these stimulated NK cells were added to firefly luciferase-expressing cancer cells and cancer cell survival was monitored with bioluminescence imaging (BLI). A drop in the BLI signal correlated with cell death. In FIGS. 7A and 7B (lower panels), IL-2-stimulated NK cells showed efficient cancer cell killing that was not affected by a CD47 blocking antibody. Thus, CD47 did not have any protective effects on these cell lines. In FIG. 7C (lower panel), however, CD47 blocking significantly increased the NK cell killing. This showed a protective effect of high CD47 on Detroit 562 against NK cells. All killing experiments with the anti-CD47 blocking antibodies were done with human FcR block to prevent antibody-dependent cellular cytotoxicity from affecting the readout. Thus, high CD47 expression correlated with an inhibitory signal that mitigated NK cell killing in cancer.

Example 5: Killing Efficacy of Human SIRPα −/−iPSC-Derived NK Cells

SIRPα −/−iPSC-derived NK cells efficiently kill CD47+ cancer cells. Human HIP iPSCs underwent CRISPR/Cas9 inactivation of both SIRPα alleles and SIRPA −/− was confirmed by Sanger sequencing. An NK cell differentiation protocol was used as previously described (bioRxiv preprint; doi: http://dx.doi.org/10.1101/614792) to generate NK cells from HIP iPSCs (iNK) and SIRPA −/−HIP iPSCs (iNK (SIRP-KO)). K562 cancer cells were made to express firefly luciferase. Some K562 were then also transduced with lentiviral particles carrying the CD47 cDNA to achieve high CD47 expression (K562-CD47OV). K562 or K562-CD47OV were used as targets in BLI killing assays as described above.

Human HIP iPSCs (B2M−/−CIITA−/−CD47tg) underwent additional gene editing to knock out the SIRPα genes. These SIRPA −/−iPSCs were then differentiated into NK cells (iNK (SIRP-KO)). iNK cells derived from human HIP iPSCs served as controls. When K562 were used as target cells, both iNKs and iNK (SIRP-KO) showed similar killing efficacy (FIG. 8A). When K562 targets overexpressing CD47 were used, the iNK (SIRP-KO) were more aggressive, while iNKs showed some reduced killing capacity (FIG. 8B). Thus, for target cells expressing protective CD47 levels, the engineered iNK (SIRP-KO) were more powerful.

IX. EXEMPLARY SEQUENCES

SEQ ID NO: 1
Human SIRPα
>NP_001317657.1 tyrosine-protein phosphatase non-receptor type substrate 1 isoform 2 precursor
[Homo sapiens]
MEPAGPAPGRLGPLLCLLLAASCAWSGVAGEEELQVIQPDKSVLVAAGET
ATLRCTATSLIPVGPIQWFRGAGPGRELIYNQKEGHFPRVTTVSDLTKRN
NMDFSIRIGNITPADAGTYYCVKFRKGSPDDVEFKSGAGTELSVRAKPSA
PVVSGPAARATPQHTVSFTCESHGFSPRDITLKWFKNGNELSDFQTNVDP
VGESVSYSIHSTAKVVLTREDVHSQVICEVAHVTLQGDPLRGTANLSETI
RVPPTLEVTQQPVRAENQVNVTCQVRKFYPQRLQLTWLENGNVSRTETAS
TVTENKDGTYNWMSWLLVNVSAHRDDVKLTCQVEHDGQPAVSKSHDLKVS
AHPKEQGSNTAAENTGSNERNIYIVVGVVCTLLVALLMAALYLVRIRQKK
AQGSTSSTRLHEPEKNAREITQVQSLDTNDITYADLNLPKGKKPAPQAAE
PNNHTEYASIQTSPQPASEDTLTYADLDMVHLNRTPKQPAPKPEPSFSEY
ASVQVPRK SEQ ID NO: 2
Human CD47
>NP_001768.1 leukocyte surface antigen CD47 isoform 1 precursor [Homo sapiens]
MWPLVAALLLGSACCGSAQLLFNKTKSVEFTFCNDTVVIPCFVTNMEAQN
TTEVYVKWKFKGRDIYTFDGALNKSTVPTDFSSAKIEVSQLLKGDASLKM
DKSDAVSHTGNYTCEVTELTREGETIIELKYRVVSWFSPNENILIVIFPI
FAILLFWGQFGIKTLKYRSGGMDEKTIALLVAGLVITVIVIVGAILFVPG
EYSLKNATGLGLIVTSTGILILLHYYVFSTAIGLTSFVIAILVIQVIAYI
LAVVGLSLCIAACIPMHGPLLISGLSILALAQLLGLVYMKFVASNQKTIQ
PPRKAVEEPLNAFKESKGMMNDE All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

---

What is claimed:

1. A population of modified Natural Killer (NK) cells, comprising a reduced Signal Regulatory Protein Alpha (SIRPα) function when compared to an NK cell population having an unmodified SIRPα function, wherein said modified NK cells effectively kill a population of cancer cells that express CD47 in an in vitro NK assay.

2. The population of modified NK cell population of claim 1, wherein said cancer cell killing occurs faster than that of said unmodified NK cell population in said assay.

3. The population of modified NK cells claim 1, wherein said modified NK cells are primary NK cells.

4. The population of modified NK cells of claim 1, wherein said reduced SIRPα function results from a genetic modification to said population of modified NK cells.

5. The population of modified NK cells of claim 4, wherein said genetic modification results from a SIRPα knockout, a regulatory sequence alteration, or a frameshift mutation.

6. The population of modified NK cells of claim 4, wherein said genetic modification was obtained using a transcription activator-like effector nuclease, clustered regularly interspaced short palindromic repeats)/Cas9 (CRISPR-Cas9), or Zinc Finger nuclease technology.

7. The population of modified NK cells of claim 1, wherein said reduced SIRPα function results from an interfering nucleic acid molecule.

8. The population of modified NK cells of claim 7, wherein said interfering nucleic acid molecule is selected from the group consisting of small interfering RNA (siRNA), antisense oligonucleotides (ASO), locked nucleic acids (LNA), splice switching oligonucleotides (SSO), and sno-derived RNA (sdRNA).

9. The population of modified NK cells of claim 1, wherein said reduced SIRPα function results from a molecule that binds to said SIRPα on the surface of said modified NK cells.

10. The population of modified NK cells of claim 9, wherein said molecule is an anti-SIRPα antibody.

11. The population of modified NK cells of claim 1, wherein said cancer is selected from the group consisting of acute myeloid leukemia, non-small cell lung cancer, urinary bladder neoplasms, hepatocellular carcinoma, melanoma, Merkel Cell carcinoma, triple negative breast cancer, ovarian cancer, renal cell carcinoma, colorectal cancer, and a sarcoma.

12. The population of modified NK cells of claim 1, wherein said NK cells are derived from an induced pluripotent stem cell (IPSC).

13. The population of modified NK cells of claim 1, wherein said NK cells are derived from an embryonic stem cell (ESC).

14. The population of modified NK cells of claim 1, wherein said NK cells comprise a chimeric antigen receptor (CAR-NK).

15. A method of treating cancer, comprising administering the population of modified NK cells of claim 1 to a subject.

16. The method of claim 15, wherein said subject is selected from the group consisting of a human, mouse, rat, cat, dog, rabbit, guinea pig, hamster, sheep, pig, horse, bovine, and non-human primate.

17. The method of claim 15, wherein said cancer is selected from the group consisting of acute myeloid leukemia, non-small cell lung cancer, urinary bladder neoplasms, hepatocellular carcinoma, melanoma, Merkel Cell carcinoma, triple negative breast cancer, ovarian cancer, renal cell carcinoma, colorectal cancer, and a sarcoma.

18. A method of making the population of modified NK cells of claim 1, comprising modifying SIRPα+ NK cells to become SIRPα− using a transcription activator-like effector nuclease, clustered regularly interspaced short palindromic repeats)/Cas9 (CRISPR-Cas9), or Zinc Finger nuclease technology.

19. The method of claim 18, wherein said SIRPα protein has at least a 90% sequence identity with SEQ ID NO:1.

20. The method of claim 19, wherein said SIRPα protein has the sequence of SEQ ID NO:1.

21. A method of making the population of modified NK cells of claim 1, comprising downregulating a SIRPα expression in said population of modified NK cells using small interfering RNA (siRNA), antisense oligonucleotides (ASO), locked nucleic acids (LNA), splice switching oligonucleotides (SSO), or sno-derived RNA (sdRNA).

22. A population of modified Natural Killer (NK) cells, comprising a reduced Signal Regulatory Protein Alpha (SIRPα) function when compared to a NK cell having an unmodified SIRPα function, wherein said modified NK cells effectively kill a population of hypoimmune cells that express CD47 in an in vitro NK assay.

* * * * *

SEQUENCE LISTING

```
<160> NUMBER OF SEQ ID NOS: 2

<210> SEQ ID NO 1
<211> LENGTH: 508
<212> TYPE: PRT
<213> ORGANISM: Homo sapiens

<400> SEQUENCE: 1

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
```

```
                    20                  25                  30
    Glu Leu Gln Val Ile Gln Pro Asp Lys Ser Val Leu Val Ala Ala Gly
                    35                  40                  45
    Glu Thr Ala Thr Leu Arg Cys Thr Ala Thr Ser Leu Ile Pro Val Gly
     50                  55                  60
    Pro Ile Gln Trp Phe Arg Gly Ala Gly Pro Arg Glu Leu Ile Tyr
     65                  70                  75                  80
    Asn Gln Lys Glu Gly His Phe Pro Arg Val Thr Thr Val Ser Asp Leu
                        85                  90                  95
    Thr Lys Arg Asn Asn Met Asp Phe Ser Ile Arg Ile Gly Asn Ile Thr
                    100                 105                 110
    Pro Ala Asp Ala Gly Thr Tyr Tyr Cys Val Lys Phe Arg Lys Gly Ser
                    115                 120                 125
    Pro Asp Asp Val Glu Phe Lys Ser Gly Ala Gly Thr Glu Leu Ser Val
                    130                 135                 140
    Arg Ala Lys Pro Ser Ala Pro Val Val Ser Gly Pro Ala Ala Arg Ala
    145                 150                 155                 160
    Thr Pro Gln His Thr Val Ser Phe Thr Cys Glu Ser His Gly Phe Ser
                        165                 170                 175
    Pro Arg Asp Ile Thr Leu Lys Trp Phe Lys Asn Gly Asn Glu Leu Ser
                    180                 185                 190
    Asp Phe Gln Thr Asn Val Asp Pro Val Gly Glu Ser Val Ser Tyr Ser
                    195                 200                 205
    Ile His Ser Thr Ala Lys Val Val Leu Thr Arg Glu Asp Val His Ser
                    210                 215                 220
    Gln Val Ile Cys Glu Val Ala His Val Thr Leu Gln Gly Asp Pro Leu
    225                 230                 235                 240
    Arg Gly Thr Ala Asn Leu Ser Glu Thr Ile Arg Val Pro Pro Thr Leu
                        245                 250                 255
    Glu Val Thr Gln Gln Pro Val Arg Ala Glu Asn Gln Val Asn Val Thr
                    260                 265                 270
    Cys Gln Val Arg Lys Phe Tyr Pro Gln Arg Leu Gln Leu Thr Trp Leu
                    275                 280                 285
    Glu Asn Gly Asn Val Ser Arg Thr Glu Thr Ala Ser Thr Val Thr Glu
    290                 295                 300
    Asn Lys Asp Gly Thr Tyr Asn Trp Met Ser Trp Leu Leu Val Asn Val
                        305                 310                 315                 320
    Ser Ala His Arg Asp Asp Val Lys Leu Thr Cys Gln Val Glu His Asp
                    325                 330                 335
    Gly Gln Pro Ala Val Ser Lys Ser His Asp Leu Lys Val Ser Ala His
                    340                 345                 350
    Pro Lys Glu Gln Gly Ser Asn Thr Ala Ala Glu Asn Thr Gly Ser Asn
                    355                 360                 365
    Glu Arg Asn Ile Tyr Ile Val Val Gly Val Val Cys Thr Leu Leu Val
                    370                 375                 380
    Ala Leu Leu Met Ala Ala Leu Tyr Leu Val Arg Ile Arg Gln Lys Lys
    385                 390                 395                 400
    Ala Gln Gly Ser Thr Ser Ser Thr Arg Leu His Glu Pro Glu Lys Asn
                        405                 410                 415
    Ala Arg Glu Ile Thr Gln Val Gln Ser Leu Asp Thr Asn Asp Ile Thr
                    420                 425                 430
    Tyr Ala Asp Leu Asn Leu Pro Lys Gly Lys Lys Pro Ala Pro Gln Ala
                    435                 440                 445
```

Ala Glu Pro Asn Asn His Thr Glu Tyr Ala Ser Ile Gln Thr Ser Pro
450                 455                 460

Gln Pro Ala Ser Glu Asp Thr Leu Thr Tyr Ala Asp Leu Asp Met Val
465                 470                 475                 480

His Leu Asn Arg Thr Pro Lys Gln Pro Ala Pro Lys Pro Glu Pro Ser
                485                 490                 495

Phe Ser Glu Tyr Ala Ser Val Gln Val Pro Arg Lys
            500                 505

<210> SEQ ID NO 2
<211> LENGTH: 323
<212> TYPE: PRT
<213> ORGANISM: Homo sapiens

<400> SEQUENCE: 2

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
                100                 105                 110

Thr Cys Glu Val Thr Glu Leu Thr Arg Glu Gly Glu Thr Ile Ile Glu
            115                 120                 125

Leu Lys Tyr Arg Val Val Ser Trp Phe Ser Pro Asn Glu Asn Ile Leu
130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

```
Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```